US009125678B2

(12) United States Patent
Lye

(10) Patent No.: US 9,125,678 B2
(45) Date of Patent: Sep. 8, 2015

(54) SURGICAL ORIENTATION SYSTEM AND ASSOCIATED METHOD

(75) Inventor: Robert Lye, Brookvale (AU)

(73) Assignee: INERTIAL ORTHOPAEDIC NAVIGATION SOLUTIONS PTY LTD, Brookvale, New South Wales (AU)

(*) Notice: Subject to any disclaimer, the term of this patent is extended or adjusted under 35 U.S.C. 154(b) by 0 days.

(21) Appl. No.: 13/119,405

(22) PCT Filed: Sep. 15, 2009

(86) PCT No.: PCT/AU2009/001213
§ 371 (c)(1),
(2), (4) Date: Mar. 16, 2011

(87) PCT Pub. No.: WO2010/031111
PCT Pub. Date: Mar. 25, 2010

(65) Prior Publication Data
US 2011/0166435 A1   Jul. 7, 2011

(30) Foreign Application Priority Data

Sep. 17, 2008  (AU) ................. 2008904826
Apr. 30, 2009  (AU) ................. 2009901865

(51) Int. Cl.
A61B 5/05   (2006.01)
A61B 19/00  (2006.01)
(Continued)

(52) U.S. Cl.
CPC .......... A61B 19/22 (2013.01); A61B 2019/4836 (2013.01); A61B 2019/507 (2013.01);
(Continued)

(58) Field of Classification Search
CPC ........... A61B 19/22; A61B 2019/5287; A61B 2019/4836; A61B 2019/507; A61B 2019/5268; A61F 2/34; A61F 2/4609; A61F 2002/4668
USPC ........................................ 606/91; 623/22.21
See application file for complete search history.

(56) References Cited

U.S. PATENT DOCUMENTS 2,535,559 A * 12/1950 Wolf .................. 5/630
5,305,203 A    4/1994 Raab
(Continued)

FOREIGN PATENT DOCUMENTS

EP      1 870 053     10/2003
WO     WO-00/30534    11/1999
(Continued)

OTHER PUBLICATIONS

Tannast et al. "Anatomic Referencing of Cup Orientation in Total Hip Arthroplasty". Clinical Orthopaedics and Related Research. No. 436, pp. 144-150. 2005.*
(Continued)

Primary Examiner — Long V Le
Assistant Examiner — Colin T Sakamoto
(74) Attorney, Agent, or Firm — Gottlieb, Rackman & Reisman P.C.

(57) ABSTRACT

The surgical orientation system is used to assist a surgeon to orient a prosthetic component relative to a patient's anatomy during surgery. An embodiment is particularly suited for assisting surgeons to locate an acetabular cup into a reamed acetabulum. The system includes: an implement (1) for releasable attachment of a prosthetic component; an electronic orientation monitor (2) attached to the implement (1); and a brace (3). The brace (3) is releasably attachable to the patient so as to define a reference point (4) relative to the patient's anatomy. This reference point (4) is external of the patient and includes at least one surface (5) defining a reference plane that is used to orient the monitor (2) into a reference orientation to calibrate the monitor (2). The surgeon then manipulates the implement (1) so that the prosthetic component is in the desired position relative to the patient and the monitor (2) provides an indication to the surgeon when a subsequent orientation of the monitor (2) has a predefined relationship relative to the reference orientation; for example the predefined relationship may be parallel to within predefined tolerances. Upon receiving the indication the surgeon inserts the prosthetic component into the patient.

18 Claims, 15 Drawing Sheets

(51) Int. Cl.
*A61F 2/34* (2006.01)
*A61F 2/46* (2006.01)

(52) U.S. Cl.
CPC . *A61B2019/5268* (2013.01); *A61B 2019/5287* (2013.01); *A61F 2/34* (2013.01); *A61F 2/4609* (2013.01); *A61F 2002/4668* (2013.01)

(56) References Cited

U.S. PATENT DOCUMENTS

| | | | |
|---|---|---|---|
| 5,921,992 | A * | 7/1999 | Costales et al. ............... 606/130 |
| 6,205,411 | B1 | 3/2001 | DiGioia, III et al. |
| 2004/0102792 | A1 | 5/2004 | Sarin et al. |
| 2004/0254584 | A1 | 12/2004 | Sarin et al. |
| 2005/0021044 | A1 | 1/2005 | Stone et al. |
| 2005/0149054 | A1 | 7/2005 | Gorek |
| 2005/0251026 | A1 | 11/2005 | Stone |
| 2006/0271199 | A1 | 11/2006 | Johnson |
| 2008/0051910 | A1 | 2/2008 | Kammerzell et al. |

FOREIGN PATENT DOCUMENTS

| | | |
|---|---|---|
| WO | WO-00/38570 | 12/1999 |
| WO | WO-02/080824 A1 | 4/2002 |
| WO | WO-03/037192 A1 | 11/2002 |
| WO | WO-2004/014219 A2 | 8/2003 |
| WO | WO-2004/112610 A2 | 6/2004 |
| WO | WO-2005/009303 A1 | 7/2004 |
| WO | WO-2005/046475 | 11/2004 |
| WO | WO-2006/079211 A1 | 1/2006 |
| WO | WO-2007/087668 A1 | 1/2006 |
| WO | WO-2007/061890 A2 | 11/2006 |
| WO | WO-2007/061890 A2 | 5/2007 |

OTHER PUBLICATIONS

DiGioia et al. "An Image Guided Navigation System for Accurate Alignment in Total Hip Replacement Surgery". CMU-RI-TR98-18. Robotics Institute, Carnegie Mellon University. 1998.*
International Search Report for PCT/AU2009/001213.

* cited by examiner

SURGICAL ORIENTATION SYSTEM AND ASSOCIATED METHOD

FIELD OF THE INVENTION

The present invention relates to surgical implements and surgical methods and in particular to an orientation system and method for use in surgical procedures, for example surgery involving prosthetic components.

BACKGROUND OF THE INVENTION

Whilst the following discussion is with respect to hip replacement surgery, a person skilled in the art will appreciate that the present invention is not limited to this particular field of use and may be adapted to use with any bone structure or various types of surgery.

Hip replacement surgery involves the use of a prosthetic cup (acetabular cup) or a prosthetic ball (femoral stems) or both to restore the ball and cup joint functionality of the hip. The ball and cup joint enables the hip to rotate in different directions to various degrees (in contrast to the relatively limited rotation of a knee joint).

In 2001, approximately 165,000 total hip replacements were performed, according to data from the American Academy of Orthopaedic Surgeons, using figures from the National Centre for Health Statistics. Historically, hip replacement (arthroplasty) surgery required up to a 40 cm (7 to 12 inches) curved incision to provide sufficient access for the surgeon to manually access and manipulate the hip and femur. A prosthetic cup was attached to the hip socket or the head of the femur removed and replaced with a prosthetic ball, or both.

After the incision is made, the ligaments and muscles are separated to allow the surgeon access to the bones of the hip joint. It is typically this part of the surgery that makes the ligaments and muscles somewhat weak after surgery. Until they heal, which often takes about a month to six weeks, the patient must follow special hip precautions to prevent dislocation of the new hip joint.

Typical steps in hip replacement surgery include the following:

Removing the Femoral Head: Once the hip joint is entered, the femoral head is dislocated from the acetabulum. Then the femoral head is removed by cutting through the femoral neck with a power saw.

Reaming the Acetabulum: After the femoral head is removed, the cartilage is removed from the acetabulum using a power drill and a special reamer. The reamer forms the bone in a hemispherical shape to exactly fit the metal shell of the acetabular component.

Inserting the Acetabular Component: A trial component, which is an exact duplicate of the patient's hip prosthesis, is used to ensure that the joint received will be the right size and fit. Once the right size and shape is determined for the acetabulum, the acetabular component is inserted into place. In the uncemented variety of artificial hip replacement, the metal shell is simply held in place by the tightness of the fit or with screws to hold the metal shell in place. In the cemented variety, a special epoxy type cement is used to "glue" the acetabular component to the bone.

Preparing the Femoral Canal: To begin replacing the femoral head, special rasps are used to shape and hollow out the femur to the exact shape of the metal stem of the femoral component. Once again, a trial component is used to ensure the correct size and shape. The surgeon will also test the movement of the hip joint.

Inserting the Femoral Stem: Once the size and shape of the canal exactly fit the femoral component, the stem is inserted into the femoral canal. Again, in the uncemented variety of femoral component the stem is held in place by the tightness of the fit into the bone (similar to the friction that holds a nail driven into a hole drilled into wooden board—with a slightly smaller diameter than the nail). In the cemented variety, the femoral canal is rasped to a size slightly larger than the femoral stem. Then the epoxy type cement is used to bond the metal stem to the bone.

Attaching the Femoral Head: The metal ball that replaces the femoral head is attached to the femoral stem.

The Completed Hip Replacement: Before the incision is closed, an x-ray is taken to make sure the new prosthesis is in the correct position.

Such surgery had a number of problems including:
a hospital stay of three days or more, post-operative pain and weeks of rehabilitation;
each cm of incision has a tenfold increase in the risks of blood clotting and infection post surgery; and
the surgeon was reliant on his experience and eye to ensure accurate placement of the cup into the three dimensional hip socket and alignment of the cup with the ball/femur to enable proper function of the joint. Misalignment may lead to post operative complication such as misalignment of the leg, incorrect leg length and/or incorrect soft tissue tension. The long term effects of misaligned prosthetic components can also include accelerated wear of the components, aseptic loosening of the components and potentially early repetition of the surgery.

Attempts to overcome these problems include:
WO 2003/037192 which discloses a jig (impaction tool) for use in bone surgery and thus enables the use of a smaller incision. For hip replacement surgery, the jig enables the use of a 4 to 7 cm (2 to 3 inch) incision, i.e. keyhole surgery. Other benefits include a shorter stay in hospital, less blood loss, less pain, fewer postoperative dislocations and faster recovery; and
WO 2005/046475 which discloses a gauge to assist the surgeon with accurate placement of a prosthetic when using a jig in keyhole surgery as the surgeon is no longer able to see the fit of the cup into the hip socket or the fit between the ball and cup.

The gauge provided in WO 2005/046475 has enabled efficient use of the impaction tool of WO 2003/037192. Commercial examples include the NilNav Hip System available from MAC Surgical. However, the gauge only works in two dimensions and there is still a heavy reliance on the surgeon's eye and experience for optimal placement of the cup into the hip.

There is thus a need to further aids to assist the surgeon during surgery.

SUMMARY OF THE INVENTION

It is an object of the present invention to overcome, or substantially ameliorate, one or more of the disadvantages of the prior art, or to provide a useful alternative.

According to a first aspect of the invention there is provided a surgical orientation system for assisting a surgeon to orient a prosthetic component relative to a patient's anatomy, the system including:
an implement for releasable attachment of a prosthetic component;
an electronic orientation monitor attachable to the implement; and a brace for releasable attachment to the patient so as to define a reference point relative to said anatomy, the reference point being disposed in use externally of the patient and being adapted for orientation of the electronic orientation monitor into a reference orientation, wherein the electronic orientation monitor is adapted to acquire reference orientation information whilst in the reference orientation, and wherein the electronic orientation monitor is adapted to acquire subsequent orientation information during manipulation of the implement whilst the implement is physically separate from the brace.

In an embodiment the electronic orientation monitor is also adapted to provide an indication when a subsequent orientation of the electronic orientation monitor has a predefined relationship relative to the reference orientation. Optionally, the electronic orientation monitor may be adapted to provide an indication so as to guide manipulation of the implement such that a subsequent orientation of the electronic orientation monitor is guided towards the predefined relationship relative to the reference orientation.

The electronic orientation monitor may include at least one of: an inertial sensor; an accelerometer; a gyroscope, a magnetometer and/or an inclinometer.

In an embodiment the reference point includes a surface defining a reference plane. This surface may be part of a docking station adapted to receive the electronic orientation monitor and to thereby orient the electronic orientation monitor into the reference orientation. In one embodiment the docking station is rotatably disposed on the brace.

In an embodiment the brace includes a movable jaw for clamping engagement with the patient. The movable jaw may be disposed at a rear end of the brace and have at least one positioning pad for clamping engagement adjacent the patient's sacrum. This embodiment also includes at least one positioning pad disposed at a front end of the brace for clamping engagement adjacent the patient's pubic crest. Two further positioning pads may be disposed at the front end of the brace for clamping engagement adjacent the patient's anterior superior iliac spine. For the embodiment having a rotatable docking station, the axis of rotation is preferably parallel to a plane containing the at least one positioning pad and the two further positioning pads.

An embodiment of the brace includes a base extending intermediate and interconnecting the front end and the rear end, said base being adapted in use to at least partially support the patient. Preferably the base comprises at least two selectively interengagable base members. An alternative embodiment dispenses with the base and instead includes an elongate frame extending intermediate and interconnecting the front end and the rear end, the elongate frame being adapted in use for disposition between the patient's legs.

According to a second aspect of the invention there is provided a method of assisting a surgeon to orient a prosthetic component relative to a patient's anatomy, said method including the steps of:

providing an implement for releasable attachment of a prosthetic component, said implement having an electronic orientation monitor disposed thereon;

releasably attaching the patient to a brace so as to define a reference point relative to said anatomy, said reference point being disposed in use externally of the patient;

using the reference point to orient the electronic orientation monitor into a reference orientation;

using the electronic orientation monitor to acquire reference orientation information whilst in the reference orientation;

manipulating the implement whilst the implement is physically separate from the brace such that the prosthetic component is adjacent said anatomy and;

using the electronic orientation monitor to provide an indication when a subsequent orientation of the electronic orientation monitor has a predefined relationship relative to the reference orientation.

An optional step associated with this method is use of the electronic orientation monitor to provide an indication so as to guide manipulation of the implement such that a subsequent orientation of the electronic orientation monitor is guided towards the predefined relationship relative to the reference orientation.

Another optional step associated with this method includes a step of ascertaining a neutral pelvic tilt angle of the patent's pelvis and rotating the reference point by an angle corresponding to the neutral pelvic tilt angle. Preferably the step of ascertaining a neutral pelvic tilt angle of the patent's pelvis includes forming an x-ray image of the patient's pelvis as viewed from the side and ascertaining from the x-ray image an angle between a line representing the vertical and a line extending from the patient's anterior superior iliac spine to the patient's pubic crest.

Any discussion of documents, acts, materials, devices, articles or the like which has been included in this specification is solely for the purpose of providing a context for the present invention. It is not to be taken as an admission that any or all of these matters form part of the prior art base or were common general knowledge in the field relevant to the present invention as it existed in Australia or elsewhere before the priority date of this application.

Throughout this specification the word "comprise", or variations thereof such as "comprises" or "comprising", will be understood to imply the inclusion of a stated element, integer or step, or group of elements, integers or steps, but not the exclusion of any other element, integer or step, or group of elements, integers or steps.

The features and advantages of the present invention will become further apparent from the following detailed description of preferred embodiments, provided by way of example only, together with the accompanying drawings.

BRIEF DESCRIPTION OF THE ACCOMPANYING DRAWINGS

DETAILED DESCRIPTION OF PREFERRED EMBODIMENTS OF THE INVENTION

Figure 1:
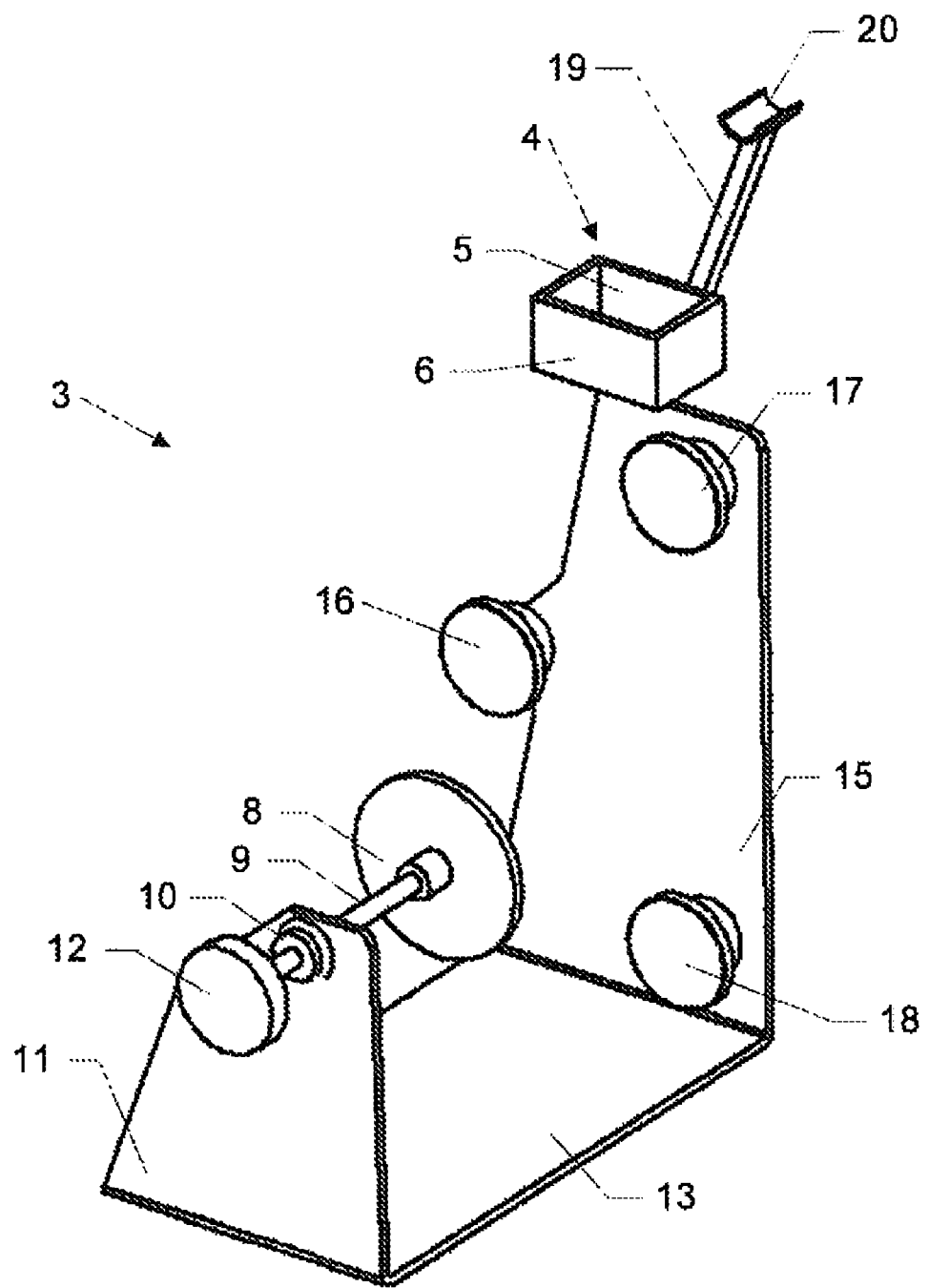
FIG. 1 is a perspective view of a brace for use as a part of the preferred embodiment of the present invention.
Figure 2:
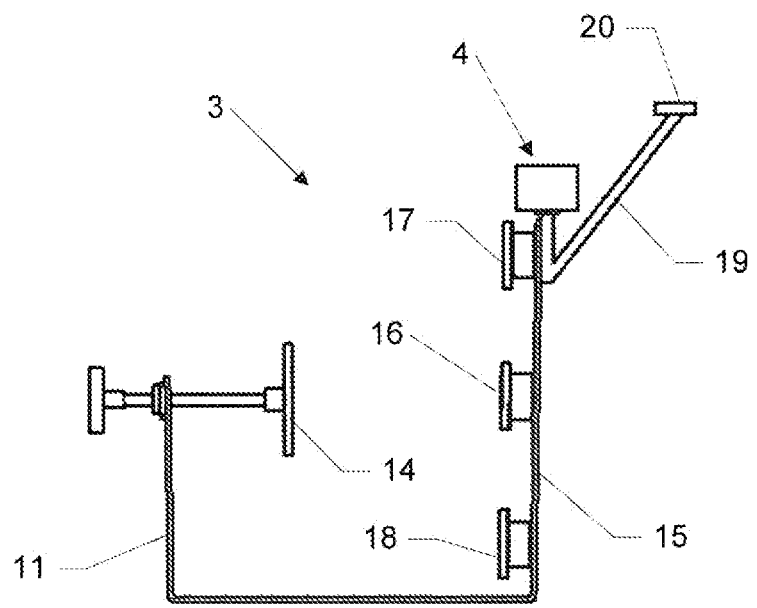
FIG. 2 is a side view of the brace of FIG. 1.
Figure 3:
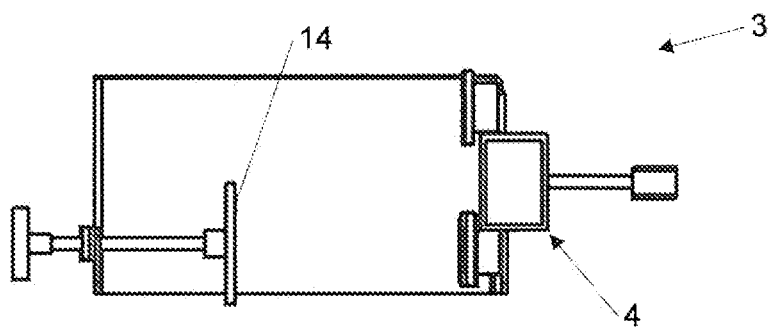
FIG. 3 is a plan view of the brace of FIG. 1.
Figure 4:
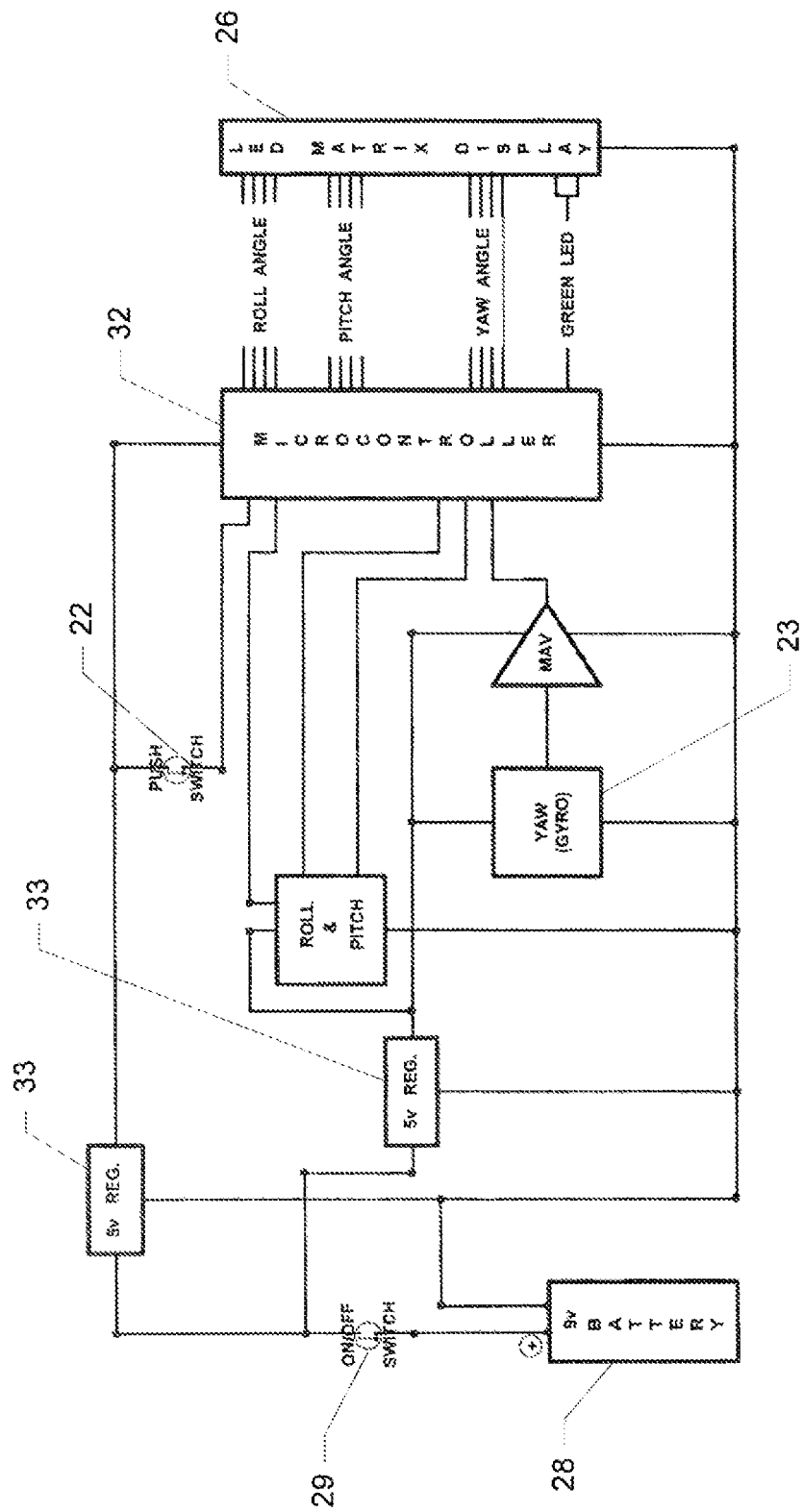
FIG. 4 is a schematic circuit layout of an electronic orientation monitor for use as a part of the preferred embodiment of the present invention.
Figure 5:
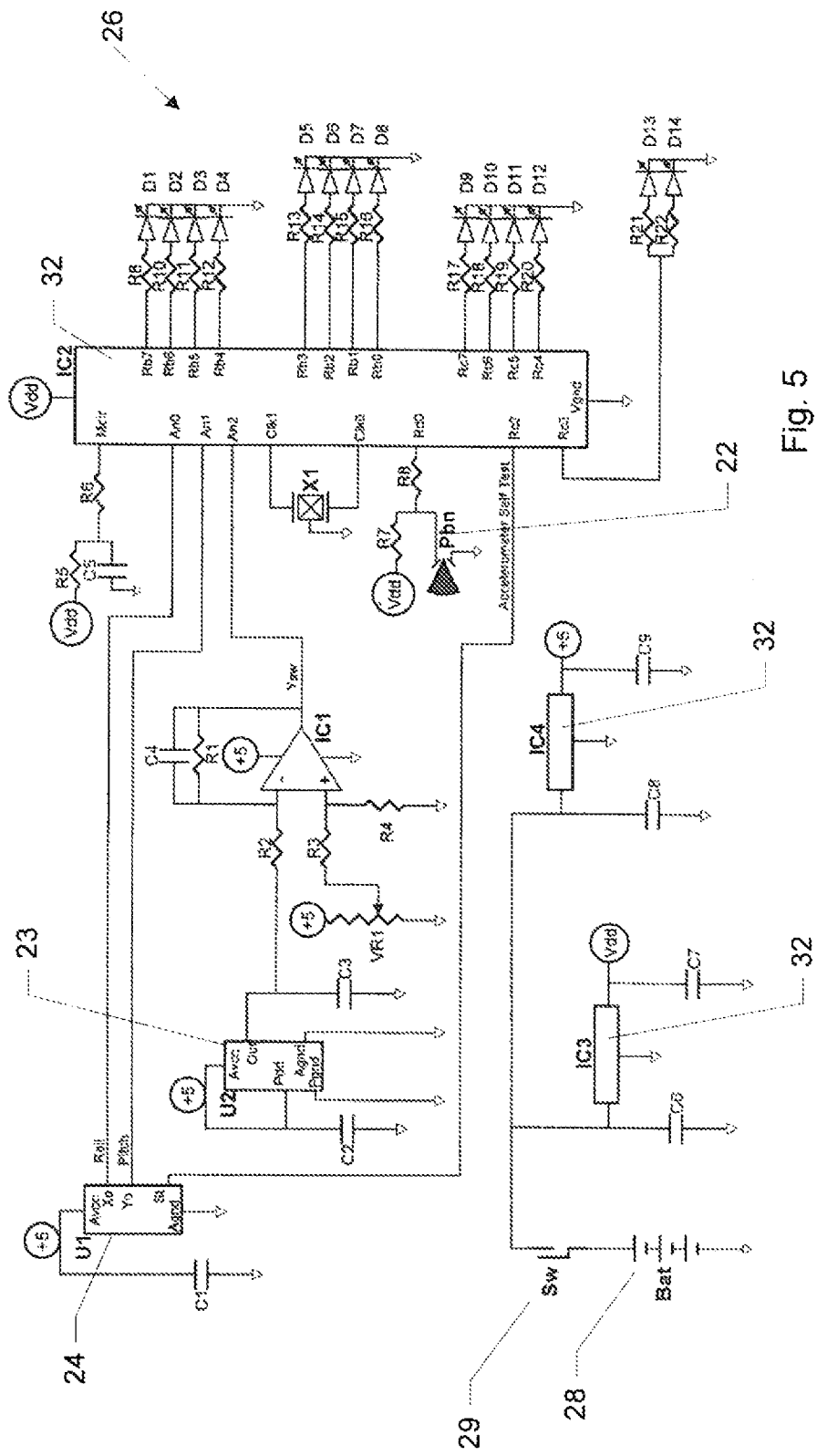
FIG. 5 is a circuit diagram of the electronic orientation monitor.
Figure 6:
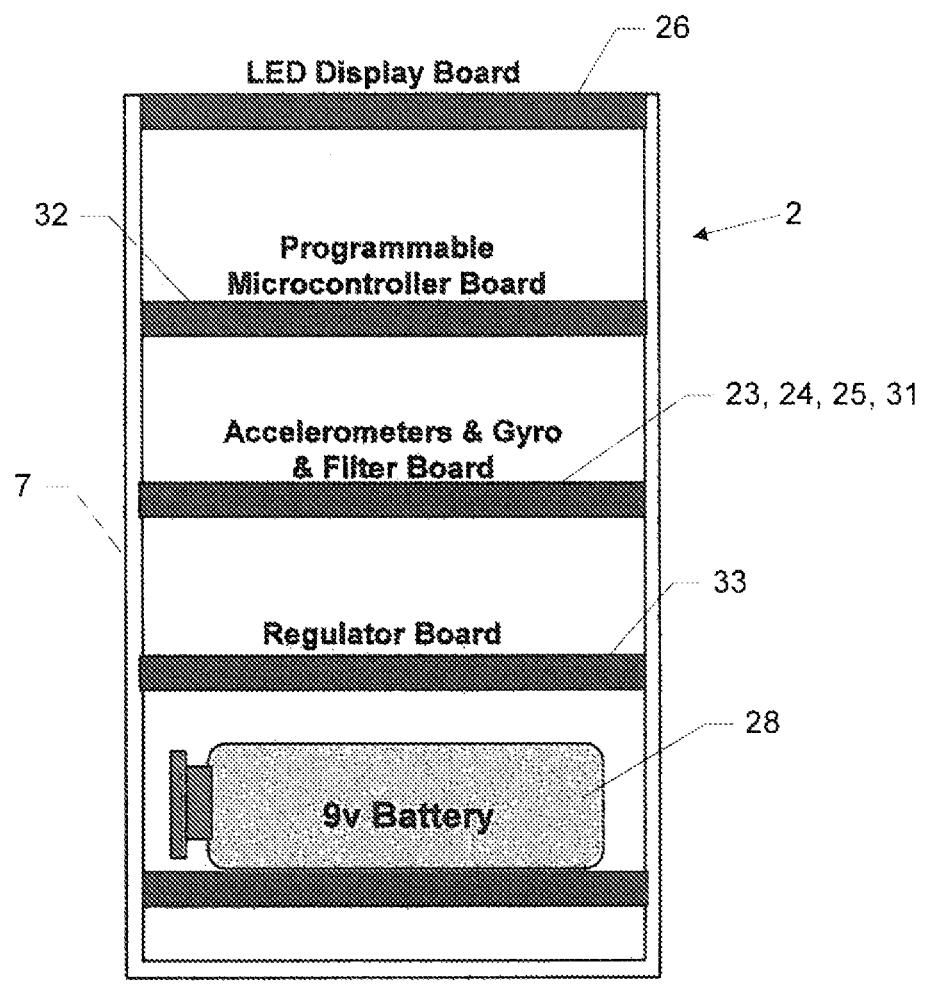
FIG. 6 is a schematic side view of the electronic orientation monitor showing the physical layout of various electrical components of the monitor.
Figure 7:
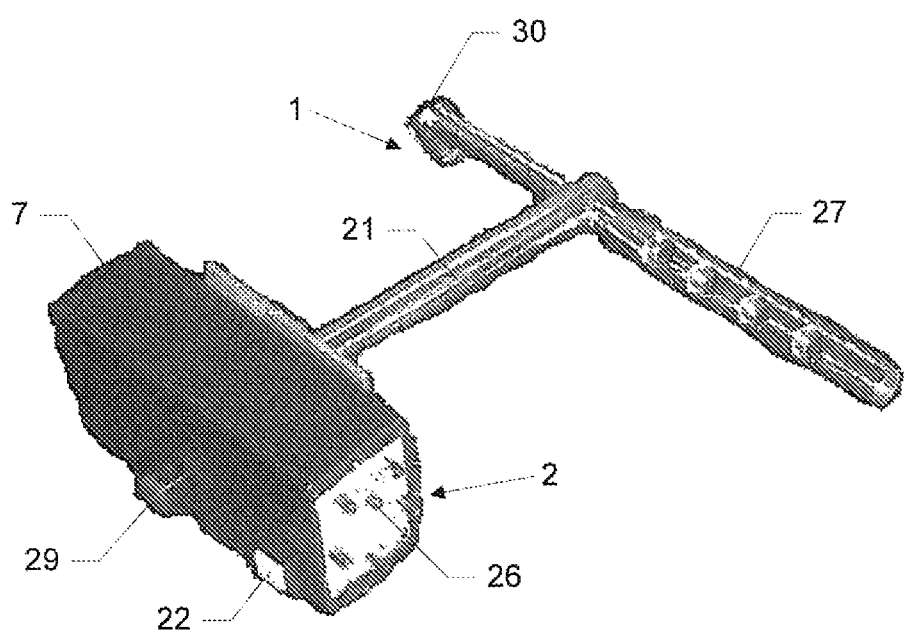
FIG. 7 is a perspective view showing an embodiment of an electronic orientation monitor attached to an implement for releasable attachment of a prosthetic component.

Referring to the drawings, the surgical orientation system of the present invention is used for assisting a surgeon to orient a prosthetic component relative to a patient's anatomy during surgery. In overview, the system comprises the following components:

an implement 1, as shown in FIG. 7, for releasable attachment of a prosthetic component;

an electronic orientation monitor 2, as shown in FIG. 7 attached to the implement 1 (a cross-section of the electronic orientation monitor 2 is shown schematically in FIG. 6 and circuit diagrams are provided in FIGS. 4 and 5); and a brace 3 as shown in FIGS. 1, 2 and 3.

The brace 3 is releasably attachable to the patient so as to define a reference point 4 relative to the patient's anatomy. This reference point 4 is external of the patient and is used to orient the electronic orientation monitor 2 into a reference orientation. Whilst in this orientation the electronic orientation monitor 2 acquires reference orientation information which is used to calibrate electronic orientation monitor 2 to the reference orientation. More particularly, the reference point 4 includes at least one surface 5 defining a reference plane. This surface 5 forms one of the internal sides of an open-topped, box-shaped docking station 6, which is dimensioned to snugly receive the electronic orientation monitor 2. This orients the electronic orientation monitor 2 into the reference orientation by abuttal of a surface of the outer casing 7 of the electronic orientation monitor 2 against the inner surface 5 and against the other inner surfaces of the docking station 6.

The preferred embodiment is particularly suited for assisting surgeons to properly locate an acetabular cup into a reamed acetabulum during hip surgery, such as total or partial hip replacements or revisions. When used in this context, the brace 3 clamps adjacent to the patient's pelvis. The patient is supported by the base 13 of the brace 3, on his or her side, with the acetabulum that is being operated upon to the top. With reference to the perspective view of the brace 3 shown in FIG. 1, the patient's head would be positioned to the right hand side of the brace 3 and the patient's feet would be positioned to the left hand side.

The brace 3 includes a movable jaw 8 which is rotatably disposed at an end of a shaft 9 that is threadedly engaged with a flange 10 disposed on a side wall 11 at the rear end of the brace 3. A manual drive wheel 12 is fixedly disposed at the opposite end of the shaft 9 to allow for screwing adjustment of the position of the movable jaw 8 relative to the side wall 11. The movable jaw 8 has a positioning pad 14 which is clamped adjacent to the patient's sacrum. Three positioning pads (16, 17 and 18) are disposed in a triangular arrangement on the opposite side wall 15 at the front end of the brace 3. Positioning pad 16 clamps adjacent to the patient's pubic crest. Positioning pads 17 and 18 clamp adjacent to the patient's anterior superior iliac spine.

Hence, once properly clamped, the brace 3 assumes a known physical relationship relative to the patient's acetabulum. It therefore follows that docking station 6 that is part of the brace 3 also assumes a known physical relationship relative to the patient's acetabulum and this known physical relationship is used along with the electronic orientation monitor 2 in subsequent surgical steps as described below to assist in the accurate orientation of the prosthetic acetabular cup relative to the reamed acetabulum.

The calibration process is typically performed whilst the electronic orientation monitor 2 is attached to the implement 1. An arm 19 extends diagonally upwardly from the front sidewall 15 of the brace 3 and has a cradle 20 disposed at a distal end. The cradle 20 is shaped for support of the elongate member 21 which connects the monitor 2 to the handle 27 of the implement 1 whilst the monitor 2 is docked in the docking station 6. Whilst the monitor 2 is docked, the surgeon or an assistant presses the calibration button 22 and the electronic orientation monitor acquires the reference orientation information required for calibration of the monitor 2 to the reference orientation. This information is dependent upon the output of a number of sensors disposed within the electronic orientation monitor 2, which are capable of monitoring the physical orientation of the monitor 2 in three dimensions.

The sensors are solid state integrated circuits (micro-machined electro mechanical systems) and include various inertial sensors such as a gyroscope 23 (ADXRS150), which provides an output signal that is dependent upon a rate of rotation about its vertical axis. To address noise and stability issues, this signal must be filtered by a filter which is built around IC1 as shown in FIG. 5. This signal is integrated over time so as to provide a yaw angle in degrees of rotation. The technique used for this integration is the multiple timebased slices version of Thomas Simpson's Rule for area under a curve.

Another inertial sensor is a dual axis accelerometer 24 (ADXL213), which functions as an inclinometer, or tilt sensor, to provide an output signal that is dependent upon the inclination of the accelerometer 24 relative to the local gravitational field. This provides roll and pitch signals which are stable and may be fed directly to the microprocessor 32 without any filtering.

In alternative embodiments other sensors may also be utilized, such as a magnetometer 25, for example, which provides an output signal that is dependent upon the direction of the local magnetic field. In other embodiments, a lesser number and/or range of types of sensors may be employed. The main issue in this regard is to ensure that the electronic orientation module 2 has a sufficient number and range of types of sensors to provide an acceptable level of spatial orientation accuracy over an acceptable time frame.

During calibration, the reference orientation information is stored within a random access memory. After calibration, during manipulation of the implement 1 (which, in turn causes re-orientation of the monitor 2 that is attached to the implement 1), the monitor 2 continues to acquire subsequent orientation information. This subsequent orientation information is compared with the stored reference orientation information and the results of the comparison are used to determine an output for display upon an array of light emitting diodes (LEDs) 26 that is disposed on a face of the monitor 2. The array of LEDs 26 is driven by the monitor circuitry as shown in FIGS. 4 and 5 to provide an indication to the surgeon when the subsequent orientation of the monitor 2 has a predefined relationship relative to the reference orientation. This indication is provided by lighting a green LED that is centrally disposed within the LED array 26.

In the preferred embodiment the predefined relationship is equality to within a predefined tolerance. However, in other embodiments other relationships, such as the current orientation forming a predefined angle relative to the reference plane to within a predefined tolerance, for example, may be utilized. The tolerance is selected dependant upon the desired sensitivity and the desired accuracy of orientation. A typical tolerance used in the preferred embodiment is to within 1, 2 or 3 degrees.

In another embodiment which dispenses with the need for a memory, the outputs of the sensors are zeroed during calibration. These outputs then assume non-zero values during subsequent manipulation of the implement 1 and attached monitor 2. During the subsequent manipulation, the sensor outputs are monitored to check whether their values return to zero (to within the relevant tolerances). When the values return to zero, it means that the monitor has assumed the reference orientation and an indication is provided to the surgeon via the green LED.

The monitor 2 is powered by a rechargeable 9 volt battery 28 and includes an on/off switch 29, one or more programmable microprocessors 32 (PIC16F877A, sold by Microchip) and one or more regulators 33. The battery 28 is recharged from an external power source via an inductive coupling arrangement. As best shown in FIG. 6, the architecture of the monitor consists of a number of electrically interconnected levels, each of which has one or more of the components required for the operation of the monitor 2. A non-limiting example of the BASIC code for programming of the microprocessor 32 is set out below in Annexure A. This programme is compiled and locked into the microcontroller 32 as protected code. The electronics for the monitor 2 are housed within a hermetically sealed outer casing 7.

The main electrical components shown in the circuit diagram of FIG. 5 are as follows:
Sensors
U1: Dual axis Accelerometer—ADXL213EB
U2: Angular Rate Gyroscope—ADXRS150EB
Integrated Circuits
IC1: CMOS Op Amp—LM6062
IC2: Micro Controller—PIC16F877A
IC3: Voltage Regulator—LM7805T
IC4: Voltage Regulator—LM78L05CZ
Resistors
R1, R4: 100 K, 0.25 W, Metal Film
R2, R3: 47 K, 0.25 W, Metal Film
R5, R7: 22 K, 0.25 W, Metal Film
R6, R8: 1 K5, 0.25 W, Metal Film
R8-R22: 100 K, 0.25 W, Metal Film
VR1: Cermet Trimpot—10 K
Capacitors
C1, C2: 10 uF, 16V, Tant
C3, C7, C9: 22 uF, 16V, Tant
C4: 1 uF, 50V, Cer
C5: 4 u 7 F, 16V, Tant
C6, C8: 100 uF, 16V, Tant
Light Emitting Diodes
D1, D4, D5, D8, D9, D12: LEDs—5 mm, Super Bright, Red
D2, D3, D6, D7, D10, D11: LEDs—5 mm, Super Bright, Yellow
D21, D22: LEDs—5 mm, Super Bright, Green
Misc
X1: Resonator—4 MHz
Pbn: Push Switch—SPST
Sw: Toggle Switch—SPST
Bat: Battery—9V Type 216

As described in the preceding paragraphs, during manipulation of the implement 1, the monitor 2 provides an indication to the surgeon when a subsequent orientation of the monitor 2 is equal to the reference orientation to within the relevant tolerance by illuminating a green LED. The relative geometry of the brace 3 (including the docking station 6, and the angle at which the acetabular cup is connected to the implement 1) is selected such that the indication is provided to the surgeon when the acetabular cup is in an anatomically desirable orientation for insertion into the reamed acetabulum. Hence, when the cup is positioned adjacent the reamed acetabulum, and the indication is given, the surgeon impacts the cup into the reamed acetabulum.

Whilst the illustrated embodiment makes use of LEDs to provide a visual indication to the surgeon, it will be appreciated that any other suitable display means may be utilized. For example, the LED array 26 may be replaced with a Liquid Crystal Display that is adapted to display an indication to assist the surgeon to achieve the desired orientation, such as an arrow, a pointer, a bubble, or the like.

In an alternative embodiment (not illustrated) the hardware used to provide a visual indication to the surgeon is not disposed on the electronic orientation monitor 2. Rather, the electronic orientation monitor 2 communicates data to drive a display on a remote display means, such as a monitor, which is preferably disposed above the patient within a convenient line of sight for the surgeon. It will be appreciated by those skilled in the art that the type of communication must be non-invasive so as to avoid interfering with other electronic equipment that may be present in the operating theatre. In one such alternative embodiment, the communication is via a wireless protocol for exchanging data over a short distance personal area network. An example of such a wireless protocol is known to those skilled in the art as "Blue Tooth". The use of a remote display such as a monitor allows for more detailed visual indications to be provided to the surgeon. It also avoids the possibility that manipulation of the implement 1 may rotate the array of light emitting diodes (LEDs) 26 that would otherwise be disposed on the electronic orientation monitor 2 out of the line of sight of the surgeon. Another advantage associated with separating the display from the electronic orientation monitor 2 is that the electronics necessary to drive the display does not have to be sterilized between operations. Such sterilization processes often involve the use of high temperatures, which may damage some of the electronic components in the display.

Yet another embodiment of the electronic orientation monitor incorporates a speaker to provide an audible indication to the surgeon to assist in the orientation process. In this embodiment the audible indication consists of a beeping noise, with the frequency of the beeping increasing as the surgeon manipulates the implement towards to the desired orientation for insertion into the reamed acetabulum. Whilst the desired orientation is being maintained to within the relevant tolerances, the beeping noise changes to a constant tone to indicate to the surgeon that the acetabulum is correctly oriented for insertion into the patient.

The assistance provided to the surgeon by the system of the preferred embodiment advantageously allows accurate orientation of the acetabular cup despite the minimal vision of the acetabulum afforded by minimally invasive surgical techniques such as "keyhole" surgery. In other words, the preferred embodiment advantageously allows for accurate orientation of the acetabular cup despite the limited visibility afforded to the surgeon through a relatively short incision.

In addition to providing the surgeon with an indication when the desired orientation is reached by illuminating the green LED as described above, the preferred embodiment also provides an indication so as to guide manipulation of the implement 1 towards the desired orientation. This minimizes the guess work and time required to manipulate the implement 1 into the desired orientation. This indication is provided via the LED display array 26, which extends in a couple of directions. Hence, if the implement 1 must be rotated in a specific rotational direction to achieve the desired orientation, then a LED indicative of that rotational direction is illuminated. The distance of the illuminated LED from the centre of the array is indicative of the amount of rotation required to achieve the desired orientation. Hence, as the implement 1 is rotated progressively closer to the desired orientation, LEDs that are progressively closer to the centre of the array 26 are illuminated. Additionally, the colour of the LED is indicative of the amount of rotation required to achieve the desired orientation, whereby red LEDs indicate that a large rotation is required and yellow LEDs indicate that a lesser amount of rotation is required. When the implement 1 is in the desired orientation (at least, to within the relevant tolerance), the central green LED is illuminated to indicate to the surgeon that the acetabular cup may be impacted into the acetabulum.

For maximum possible accuracy, the monitor 2 should not be moved around more than necessary once it has been calibrated. Additionally, the time between calibration and receiving the indication to impact the acetabular cup should be minimized. Both of these precautions help to avoid orientational inaccuracies that may otherwise creep into the functioning of the electronics in the monitor 2. If, for some reason, the monitor 2 is moved excessively after calibration, or if there is a temporal delay prior to its use, accuracy may be restored by simply re-calibrating the monitor 2.

As an alternative to the monitor 2 described above, different electronic orientation monitors may be used in other embodiments of the present invention. For example, the monitor that is disclosed in International Patent Application No. PCT/US2004/018244, published on 29 Dec. 2004 under publication number WO 2004/112610, may be used. The contents of WO 2004/112610 are hereby incorporated in their entirety by way of reference.

In summary, use of the preferred embodiment of the present system as illustrated in FIGS. 1 to 6 to assist a surgeon to orient a prosthetic component relative to a patient's anatomy involves the following steps (whether in the order shown, or otherwise):

Releasably attaching a prosthetic component and the electronic orientation monitor 2 to the implement 1. This is achieved using the connector 30 that is disposed at a distal end of the handle 27;

Clamping the patient to the brace 3 so as to define an external reference point 4 relative to the patient's anatomy;

Using the reference point 4 to orient the electronic orientation monitor 2 into a reference orientation;

Calibrating the electronic orientation monitor 2 by acquiring reference orientation information whilst the monitor 2 is in the reference orientation;

Manipulating the implement 1 whilst the implement is physically separate from the brace such that the prosthetic component is adjacent the relevant anatomy;

Using the electronic orientation monitor 2 to provide an indication so as to guide manipulation of the implement 1 such that the implement 1 is guided towards a predefined relationship relative to the reference orientation; and Using the electronic orientation monitor 2 to provide an indication when the subsequent orientation of the monitor 2 has a predefined relationship relative to the reference orientation.

One potential difficulty that may be experienced with use of the brace 3 as illustrated in FIGS. 1 to 3 is positioning of the patient across the solid base 13. Typically the brace 3 is firstly placed onto a surface such as a bed such that the base 13 is supported by the bed. The patient, who may be anesthetized at this point, is then lifted onto the base 13. This can be difficult, particularly if the patient is unconscious and therefore unable to assist in the movement process. An alternative embodiment (not illustrated) of the brace at least partially addresses this problem by splitting the base in half to form two selectively interengagable base members. Mechanical interengagement means are provided on the ends of the base members. This allows the patient to be firstly placed onto the bed and secondly each base member may be slid under the patient from either side. When they meet, the mechanical interengagement means on the two base members interengage to form a rigid base. Once the surgery is concluded, the two base members are selectively disengaged from each other and slid out from either side of the patient.

Figure 9:
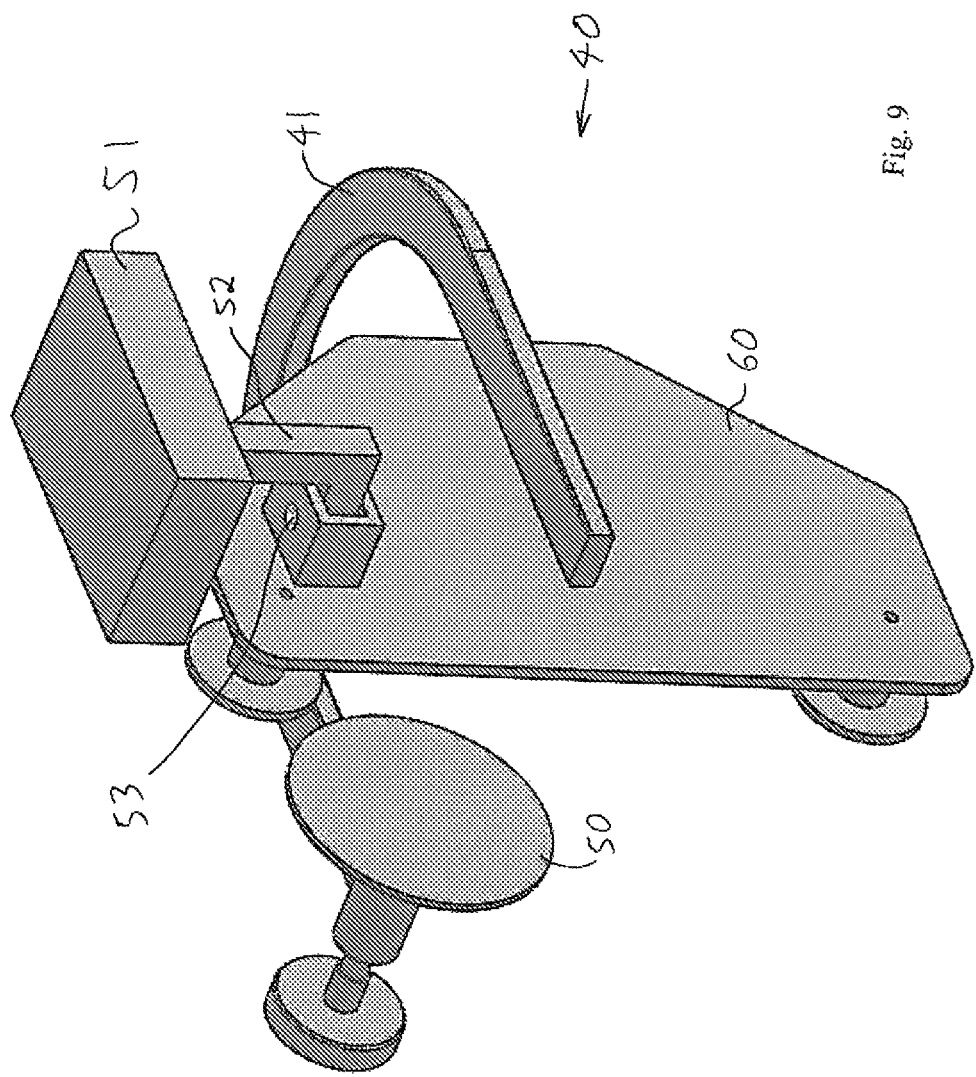
FIG. 9 is a perspective view of an alternative embodiment of a brace.
Figure 10:
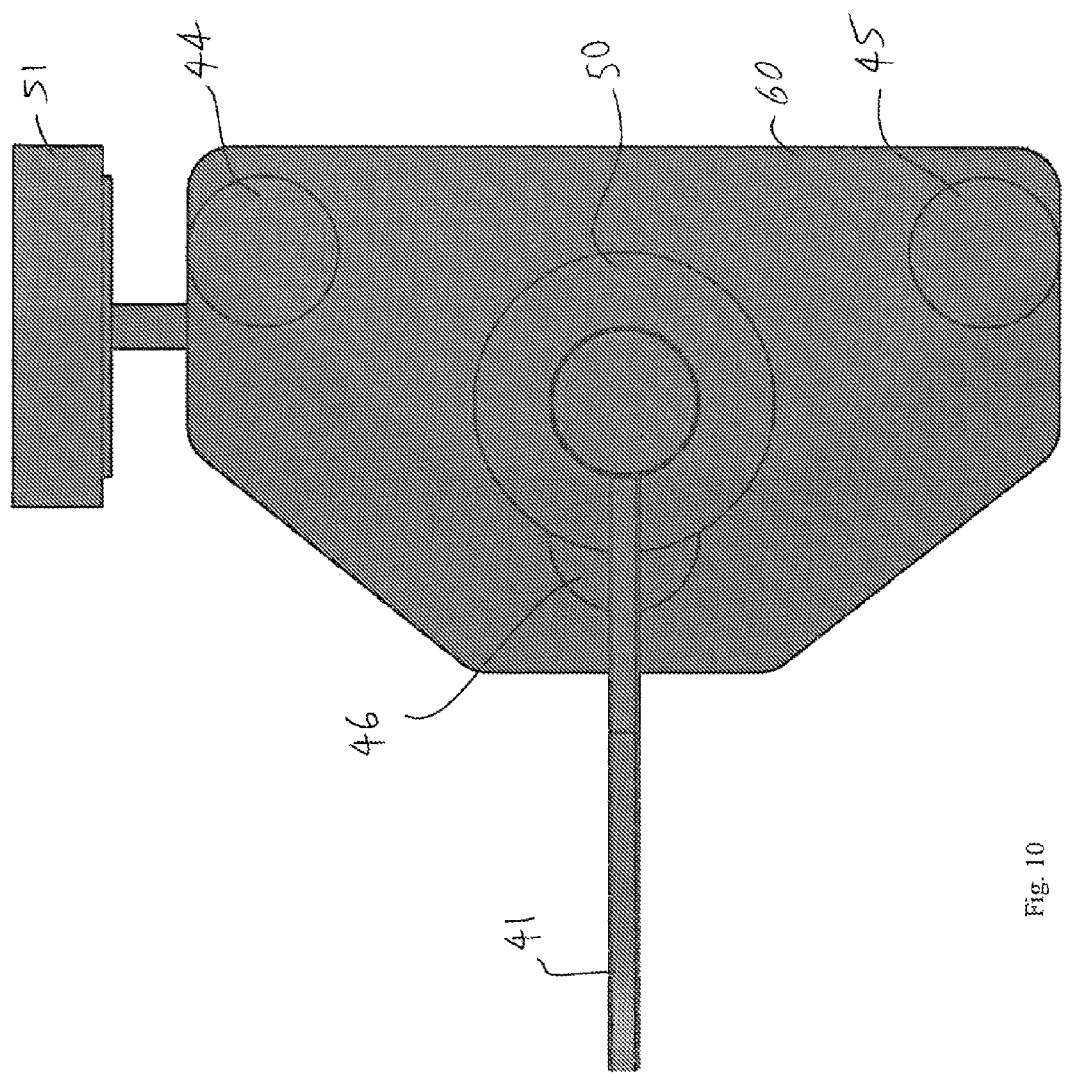
FIG. 10 is a left-side view of the brace of FIG. 9.
Figure 11:
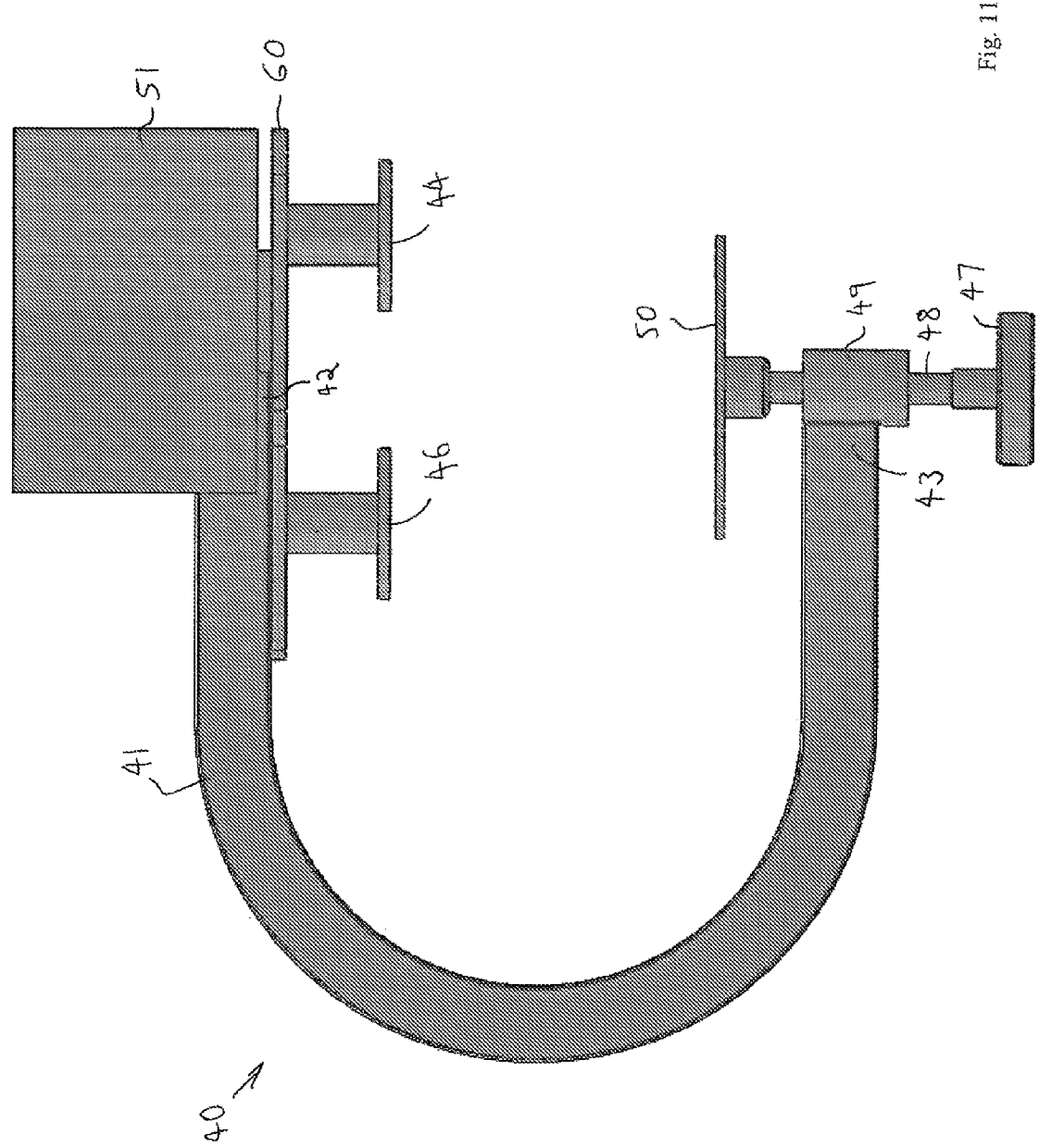
FIG. 11 is a plan view of the brace of FIG. 9.
Figure 12:
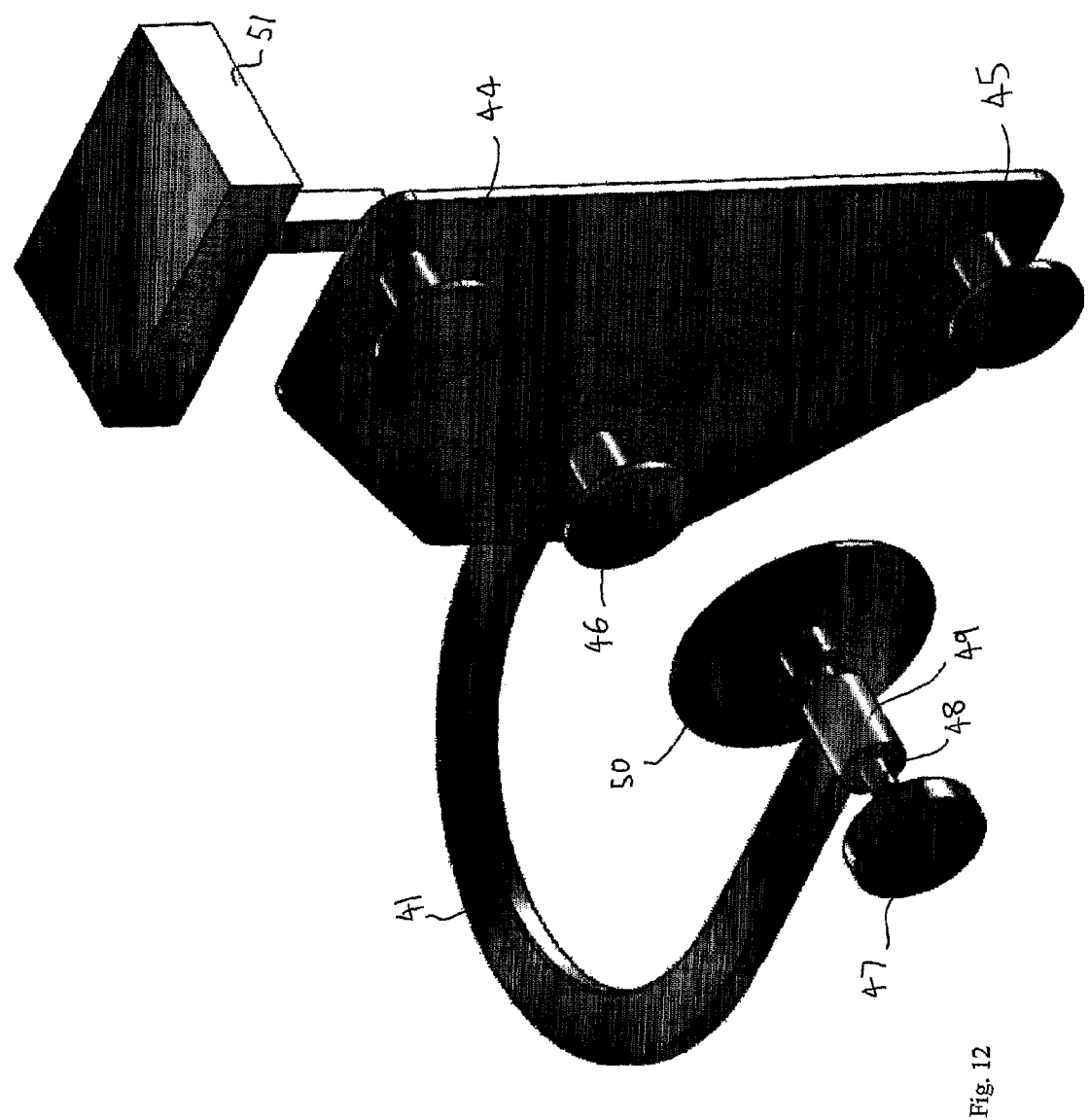
FIG. 12 is another perspective view of the brace of FIG. 9.

An alternative embodiment of the brace, as illustrated in FIGS. 9 to 11, provides another option for addressing the difficulty in placement of a patient onto the brace of FIGS. 1 to 3. In this embodiment of the brace 40, an elongate frame 41 extends intermediate and interconnects the front end 42 and the rear end 43 of the brace 40. In one such embodiment the frame has a generally rectangular cross section, with dimensions of approximately 25 mm by 10 mm. Due to its narrow dimensions, the frame 41 may be positioned so as to extend between the patient's legs. Hence, using this embodiment of the brace 40, the patient is firstly placed on the bed and secondly the brace 40 is positioned between the patient's legs. At this point the pads 44 and 45 are placed in contact with the patient's anterior superior iliac spine and the pad 46 is placed in contact with the patient's pubic crest. Each of pads 44, 45 and 46 are mounted on a plate 60, which is connected to the front end 42 of the frame 41. The handle 47 is then used to rotate externally threaded shaft 48 within internally threaded boss 49 so as to displace pad 50 toward the patient so as to clampingly engage the patient's sacrum. The boss 49 is connected to the rear end 43 of the frame 41.

The embodiment of the brace 40 as illustrated in FIGS. 9 to 11 also solves a second problem that may be associated with the embodiment illustrated in FIGS. 1 to 3. That is, with the embodiment illustrated in FIGS. 1 to 3, the broad flat base 13 defines the orientation of the brace 3 as it rests flat on the bed. This may be undesirable, particularly if the patient moves but the geometry of the base 13 doesn't allow the brace 3 to move with the patient. However, it is not necessary for any part of the brace 40 as illustrated in FIGS. 9 to 11 to be supported by the bed. Rather, the position and orientation of the brace 40 whilst in use is substantially defined by the patient's pelvic region to which it is clamped.

Another potential issue that may be associated with the embodiment of the brace 3 as illustrated in FIGS. 1 to 3 relates to patients who have a natural tilt to their pelvis, either forwards or backwards. In practice, pelvic tilt angles may typically range between −10° to +10°; although in some more extreme cases the angle may fall outside of this range. The brace 3 as illustrated in FIGS. 1 to 3 has been designed for use with patients having a vertically aligned pelvis (i.e. a pelvis which, when in the neutral position and when viewed from the side, has the pubic crest in vertical alignment with the anterior superior iliac spine). Hence, if this brace 3 is used for a patient who has a significant pelvic tilt, then the resulting hip joint may suffer due to mis-alignment of the prosthetic femoral head with the prosthetic ascetabular cup. This issue is addressed by the brace 40 as illustrated in FIGS. 9 to 11. In this brace 40, the docking station 51 is rotatably disposed on the brace 40. As best shown on FIG. 9, the docking station 51 is mounted on an arm 52, which is rotatably connected to the rest of the brace 40 via pin 53. The pin 53 defines the axis of rotation of the arm 52 and of the docking station 51. This axis of rotation is parallel to a plane containing positioning pads 44, 45 and 46.

Figure 8:
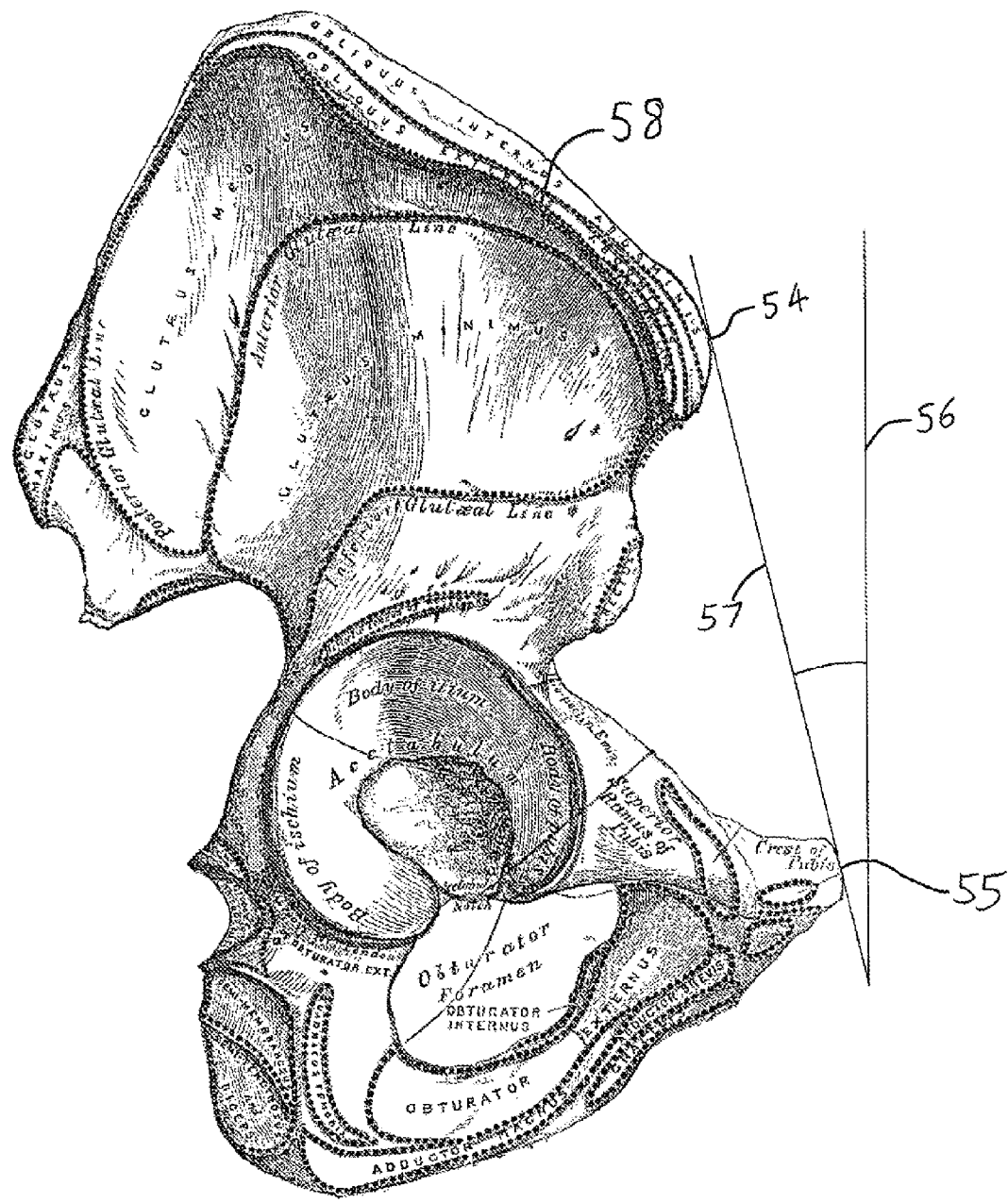
FIG. 8 is a schematic side view depicting a measurement of a patient's angle of pelvic tilt.

In use, the surgeon firstly ascertains the neutral pelvic tilt angle of the patent's pelvis by forming an x-ray image of the patient's pelvis as viewed from the side. This x-ray image is formed whilst the patient stands with their pelvis held at a neutral and comfortable tilt angle (i.e. the patient is asked not to deliberately tilt their pelvis either forwards or backwards). The pelvis in such an image is likely to appear similar to the pelvis 58 depicted in FIG. 8. The patient's pelvic tilt angle is ascertained from the x-ray image by measurement of the angle between a line 56 representing the vertical and a line 57 extending from the patient's anterior superior iliac spine 54 to the patient's pubic crest 55, as shown on FIG. 8.

Once patient's pelvic tilt angle has been ascertained, the reference point of the brace 40, which is in the form of docking station 51, is rotated by the ascertained angle. In some such embodiments an angular scale is depicted adjacent to the pin 53 for ease of reference whilst rotating the docking station 51. Once the docking station has been rotated by the required angle, the brace 40 is used in the remaining surgical steps in manner described above with reference to the brace illustrated in FIGS. 1 to 3. However, rather than providing a fixed reference that is only suitable for a vertically aligned pelvic (as is the case for brace 3), the docking station 51 of brace 40 provides a reference that has been tailored to the patient's individual requirements as dictated by the measurement of their pelvic tilt.

Figure 13:
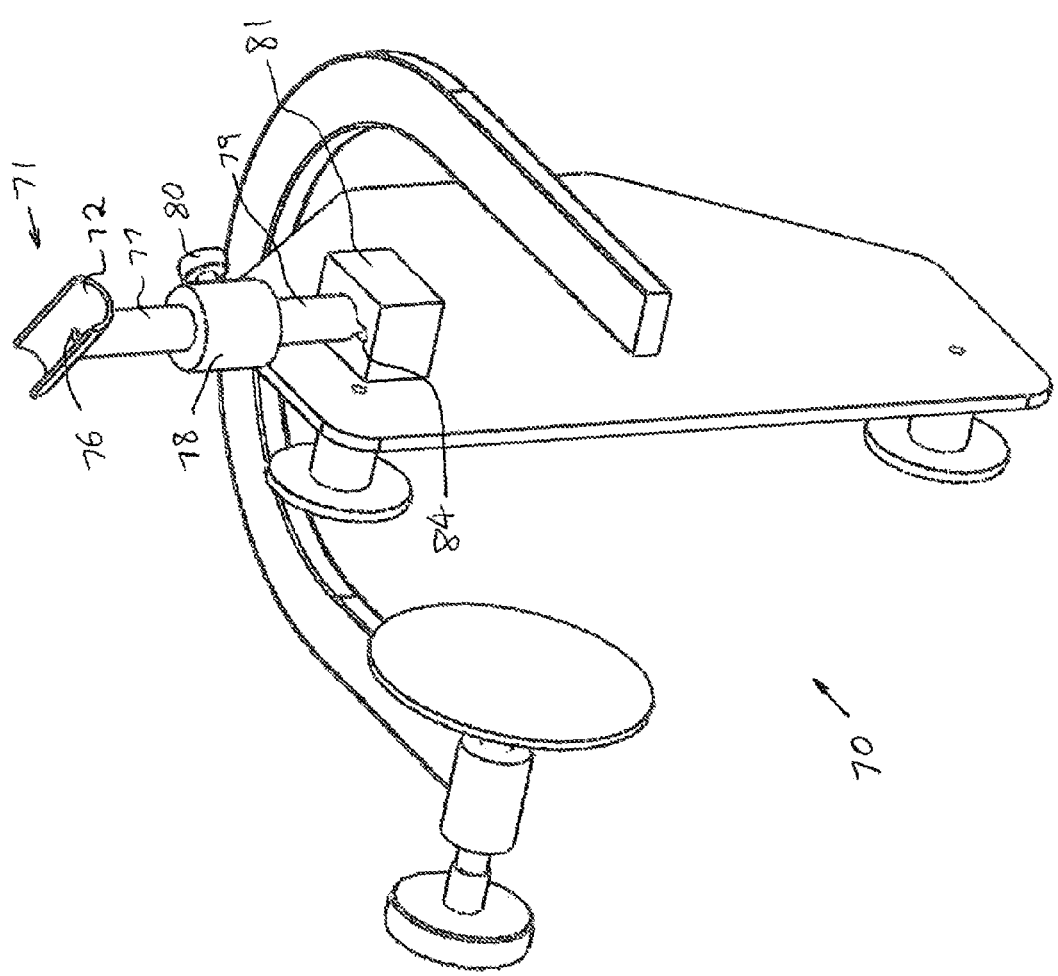
FIG. 13 is a perspective view of another embodiment of a brace.
Figure 14:
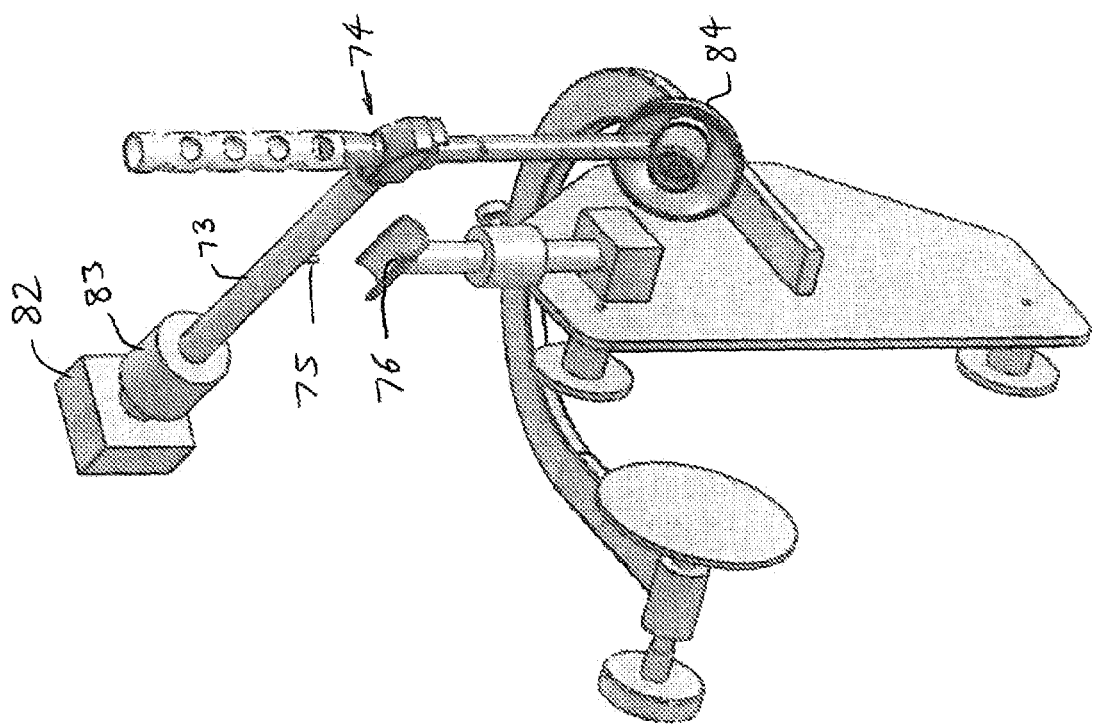
FIG. 14 is a perspective view of the embodiment of the brace from FIG. 13, along with an implement for releasable attachment of a prosthetic component.
Figure 15:
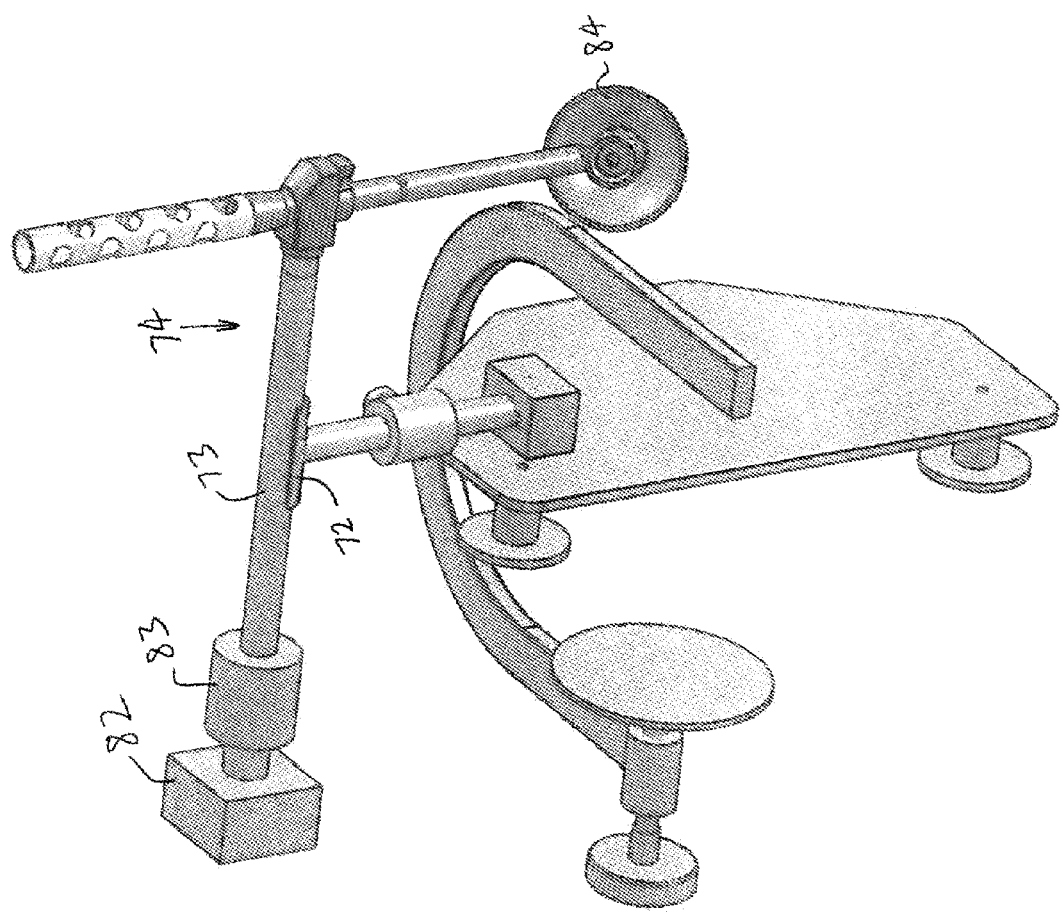
FIG. 15 is another perspective depiction of the brace and implement shown in FIG. 14.

The brace 70 illustrated in FIGS. 13 to 15 is generally similar to that shown in FIGS. 9 to 12, with the exception of the docking station 71 and the manner in which the docking station 71 is attached to the remainder of the brace 70. In this embodiment the docking station 71 takes the form of a half-cylindrical cradle 72, which is shaped to receive a correspondingly cylindrically shaped member 73 of the implement 74. As best shown in FIG. 14, a lug 75 protrudes from the member 73 so as to mate with an aperture 76 that is disposed in the cradle 72. These components are aligned such that when the member 73 is in the cradle 72 and the lug 75 is in the aperture 76, the implement 74 is in the reference orientation with respect to the patient to whom the brace 70 is clamped. This allows for calibration of the electronic orientation monitor 82 to take place in the manner outlined above with regard to the above-described embodiments.

The channel 72 of the docking station 71 is disposed on a first shaft 77. A locking means 78 connects the first shaft 77 to a second shaft 79. Loosening of the knob 80 of the locking means 78 allows the first shaft 77 to rotate relative to the second shaft 79. This rotation of the first shaft 77 causes rotation of the cradle 72 relative to the remainder of the brace 70 about an axis of rotation that is parallel to the central longitudinal axis of the first and second shafts 77 and 79. Such rotation allows for adjustment to compensate for the patient's pelvic tilt, in the manner outlined in more detail above. When the cradle 72 is at the desired angle, the knob 80 is tightened such that the locking means 78 resists any further relative rotation between the first and second shafts 77 and 79 and the angular disposition of the cradle 72 is therefore fixed relative to the remainder of the brace.

The end of the second shaft 79 is releasably attachable to the remainder of the brace 70 via attachment mechanism 81. More particularly, a projection on the end of the second shaft 79 is keyed into a slot 84 on the attachment mechanism 81 so as to resist rotation of the second shaft 79 relative to the attachment mechanism 81. Once the electronic orientation monitor 82 has been calibrated, the implement 74 may be removed from the cradle 72 and the second shaft 79 may be detached from the attachment mechanism 81. This removes the following components from the brace 70: the second shaft 79, the locking means 78, the first shaft 77 and the cradle 72. Removal of these components allows the surgeon additional room to move and thereby lessens the risk of the surgeon accidentally bumping or snagging any of the detached components whilst performing the remainder of the operation.

The implement 74 that is depicted in FIGS. 14 and 15 is adapted for use in some minimally invasive surgical techniques. The electronic orientation monitor 82 of this implement 74 is attached to the member 73 via a lockable universal joint 83, for example a ball joint. Hence, when the lockable universal joint 83 is unlocked, the electronic orientation monitor 82 may be manipulated into a desired orientation, for example in order to ensure that the display array 26 will be visible to the surgeon whilst inserting the acetabular cup 84 into the patient's reamed acetabulum. It will be appreciated that such manipulation of the electronic orientation monitor 82 should only take place prior to the calibration process. Once the electronic orientation monitor 82 has been calibrated, the lockable universal joint 83 should remain locked until such time as the prosthetic component 84 has been inserted into the patient. If the lockable universal joint 83 is accidentally unlocked after calibration, the lockable universal joint 83 should be re-locked and the calibration process commenced afresh.

In another embodiment (not illustrated) the display array 26 is tiltably mounted on the electronic orientation monitor 2. This allows for adjustment of the angle from which the display array 26 may be viewed without requiring re-orientation of the remainder of the electronic orientation monitor 2.

Figure 16:
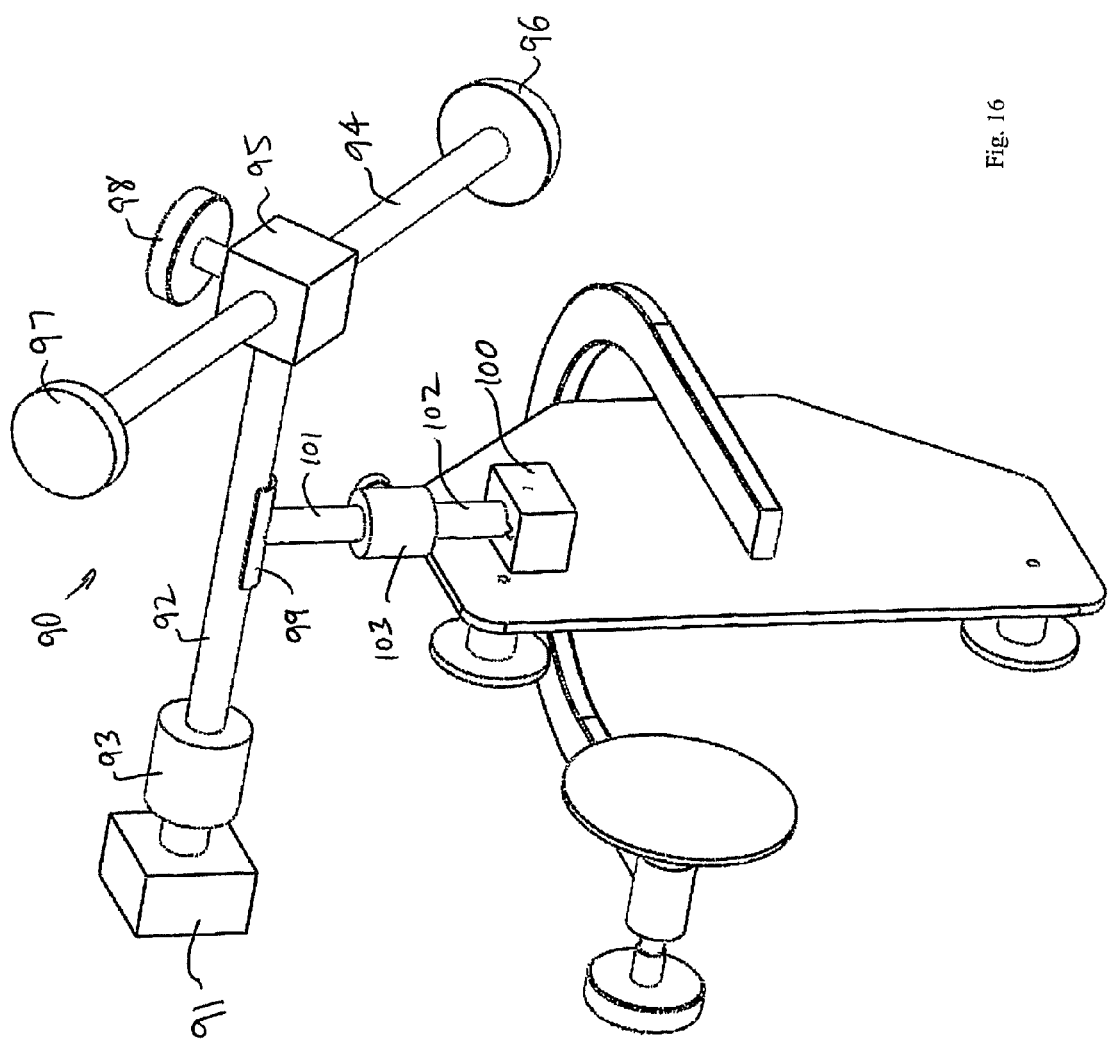
FIG. 16 is a perspective view of yet another embodiment of a brace with yet another embodiment of an implement for releasable attachment of a prosthetic component.

Turning now to the final embodiment depicted in FIG. 16, the brace is identical to that shown in FIGS. 13 to 15, however the implement 90 differs. In this embodiment the implement 90 is adapted for use in traditional open hip replacement surgical procedures. The electronic orientation monitor 91 is attached to a first member 92 via a lockable universal joint 93 that performs the same function as the lockable universal joint 83 which was described in relation to the preceding embodiment.

The first member 92 is attached to a second member 94 via a lockable angular adjustment mechanism 95 having a locking releasement knob 98. The prosthetic component, in the form of acetabular cup 96, is releasably attachable to a distal end of the second member 94. An impaction surface 97 is disposed on the proximal end of the second member 94.

Loosening of the locking releasement knob 98 unlocks the angular adjustment mechanism 95. This allows for rotation of the second member 94 about an axis of rotation that is parallel to the elongate axis of the first member 92. Rotation about this axis allows for adjustment of the abduction angle at which the acetabular cup 96 is to be inserted into the patient. Unlocking of the angular adjustment mechanism 95 also allows for rotation of the second member 94 about an axis of rotation that is parallel to the central axis of the locking releasement knob 98.

Rotation about this axis allows for adjustment of the anteversion angle at which the acetabular cup 96 is to be inserted into the patient. Once these angles have been set to their desired settings, the knob 98 is tightened to ensure that the angular adjustment mechanism 95 maintains the first and second members 92 and 94 in the desired angular configuration.

Next the surgeon calibrates the electronic orientation monitor 91 to establish the reference orientation. The surgeon then moves the implement 90 and detaches the cradle 99, the first and second shafts 101 and 102 and the locking means 103 from the attachment mechanism 100 to provide extra room to move. The acetabular cup 96 is then positioned adjacent the patient's reamed acetabulum and the orientation of the implement 90 is manipulated in accordance with the indication provided by the display array 26. Once the subsequent orientation of the monitor 91 is equal to the reference orientation to within the relevant tolerance, the monitor 91 provides an indication to the surgeon, who then impacts a hammer against impaction surface 97 so as to impact the acetabular cup 96 into the patient's reamed acetabulum.

Once the operation has been completed it is typically necessary to sterilise the equipment so as to prepare for the next operation. One method for performing such sterilisation is to place the equipment into an autoclave and heat it to a suitable temperature and pressure for a pre-determined time period, for example 132° C. at 30 psi for 10 minutes. In order for the electronics contained within the electronic orientation monitor 2 to survive being heated to this temperature some embodiments utilise outer cases that are heat-proof or heat-resistant. This may also involve providing thermal insulation at or near to the outer casing. An alternative or additional approach to providing the heat resistance is to select the individual electronic components that are used within the electronic orientation monitor 2 from amongst components that are known to have a higher than average heat tolerance.

While a number of preferred embodiments have been described, it will be appreciated by persons skilled in the art that numerous variations and/or modifications may be made to the invention without departing from the spirit or scope of the invention as broadly described. The present embodiments are, therefore, to be considered in all respects as illustrative and not restrictive.

Annexure A—BASIC Code for Programming of the Microprocessor

```
'HIGS PROGRAM V1.043'
'PURPOSE: HIGS Proof of Concept Prototype Control Program'
'NOTE 1: Uses boundary limits exclusion zone to reduce the Z axis zero drift problem'
'Port A pins 0 & 1 are default ADC input for X & Y axis analog input signals'
'Port A pin 2 is default ADC input for Z axis'
'Port A pin 3 is default ADC input for stability reference signal'
'Port B is default Output port for the X & Y axis LEDs'
'Port C I/O direction is -all pins are outputs-'
'Port C pin 3 is for the Green LED'
'Port C pins 4,5,6,7 are for the Z axis LEDs'
'Port D Pin0 is default input port for the Start/Stop pushbutton'
'The outer limits for X axis red LED on/off = w0 (+/−) 10 ADC counts'
'The inner limits for X axis yellow LED on/off = w0(+/−) 4 ADC counts'
'The outer limits for Y axis red LED on/off = w1 (+/−) 10 ADC counts'
'The inner limits for Y axis yellow LED on/off= w1 (+/−) 4 ADC counts'
'The outer limits for Z axis red LED on/off = w2 (+/−) 2000 ADC counts within each for/next loop'
'The inner limits for Z axis yellow LED on/off= w2 (+/−)35 ADC counts within each for/next loop'
'*********************************Initialise after Reset*********************************************'
init:     let dirsc = %11111111           'set Port C direction to output on all pins'
          let pinsc = %00000000           'set all Port C pins to lo (Green LED & tilt self test off)'
          let pins = %00000000            'set all Port B pins to lo (all LEDs off)'
'********************************end of initialise routine*******************************************'
'*************************Verify and Warm Up before running tests ***********************************'
vrfy:     let pins = %11111111            'show all X & Y axis LEDs'
          let pinsc = %11111000           'show Z axis and Green LEDs'
          pause 5000                      'pause 5000mSecs'
          let pins = %00000000            'switch OFF all X & Y axis LEDs'
          let pinsc = %00000000           'switch OFF Green LED and Z axis LEDs'
'**** now do 30 secs exercise to warm up the gyro and tilt systems *****'
'**** then acquire docking station data ****'
wup:      for b10 = 1 to 100              'do 100 useless loops to warm up'
          readadc10 0, w0                     'acquire X axis signal'
          poke $C0,b0                         'put Xaxis LSB into cold storage'
          poke $C1,b1                         'put Xaxis MSB into cold storage'
          readadc10 1, w0                     'acquire Y axis signal'
          poke $C2,b0                         'put Yaxis LSB into cold storage'
          poke $C3,b1                         'put Yaxis MSB into cold storage'
          readadc10 2, w0                     'acquire Z axis signal'
          poke $C4,b0                         'put Zaxis LSB into cold storage'
          poke $C5,b1                         'put Zaxis MSB into cold storage'
          let pinsc = %11110000           'show all Z axis LEDS'
          pause 125                           'pause for 125mSecs'
          let pinsc = %00000000           'switch OFF Z axis LEDs'
          pause 125                           'pause for 125mSecs'
          next b10                            'continue until all done'
          let w3 = 0                          'clear the Z axis error accumulator'
          for b10 = 1 to 64                   'accumulate 64 Zaxis acquisitions'
          readadc10 2, w6                     'get Z axis signal and store it in w6'
          let w3 = w3+w6                  'add to total in w3'
          next b10                            'continue until all done'
          let w6 = w3/64                  'get Z axis docking station average'
```

```
            let w1 = w6+5              'calculate Zaxis Notes Band Top Limit'
            let w2 = w6−1              'calculate Zaxis Notes Band Base Limit'
            let w6=w6+1                    'adjust Z axis dock for drift compensation'
            poke $C4, b12           'put Zaxis LSB into cold storage'
            poke $C5, b13           'put Zaxis MSB into cold storage'
            poke $C6, b2            'put Zaxis LSB NBTL into cold storage'
            poke $C7, b3            'put Zaxis MSB NBTL into cold storage'
            poke $C8, b4            'put Zaxis LSB NBBL into cold storage'
            poke $C9, b5            'put Zaxis MSB NBBL into cold storage'
            let w3 = 32768          'set the initial Zerr value to midpoint(32768)'
            poke $CA,b6                'put Zerr LSB into cold storage'
            poke $CB,b7                'put Zerr MSB into cold storage'
            high portc 3            'ready to go, so switch ON green LED'
            serixd("Docking Station
            Values:",13,10)
            gosub send
            gosub pbtn                    'wait for pushbutton before commencing test'
            let pins=%11111111      'switch ON all X & Y axis LEDs'
            pause 500                  'pause for 500mSecs'
            let pins=%00000000      'switch OFF all X & Y axis LEDs'
            let pinsc=%00001000     'switch ON Green LED and switch OFF Z axis LEDs'
'*******************************Start of Main Program**********************************************'
'****assumes all Variables are available for each axis routine *****'
'****w0=docking value: w1=NBTL; w2=NBBL; w3=error accumulator; w4=b6, b9; w5=b10, b11; w6=current value'
'****b6=Z axis inner loop counter; b9= unused loop counter; b10=reserved for Xaxis flag; b11=reserved for Yaxis OK flag'
'**** Zaxis dock value is resident in w0 during Zaxis subroutine*****'
'**** Zaxis NBTL value resides in w1 during Zaxis subroutine*****'
'**** Zaxis NBBL value resides in w2 during Zaxis subroutine*****'
'***Zerr and LEDs routines take approx 25 mSecs including the sertxd instruction'
'************************commence the main data acquisition routine*********************************'
main: gosub Zgo
Xgo:        low 0                   'switch OFF the X axis LEDs only'
            low 1                   'switch OFF the X axis LEDs only'
            low 2                   'switch OFF the X axis LEDs only'
            low 3                   'switch OFF the X axis LEDs only'
            peek $C0,b0             'fetch Xaxis LSB docking value from cold storage'
            peek $C1,b1             'fetch Xaxis MSB docking value from cold storage'
            readadc10 0, w6         'get new X axis data into w6'
x1:         let w1=w0+4             'calculate inner limits'
            let w2=w0−4             'calculate inner limits'
            if w6>=w1 then goto x2  'if small right tilt skip to x2'
            if w6<=w2 then goto x3  'if small left tilt skip to x3'
            b10=0                      'clear the green LED error flag'
            goto bchk
x2:         high 2                  'load right-yellow-LED-ON data'
            let w1=w0+10            'get the right tilt outer limit'
            if w6<w1 then goto Xxx  'if within the limit adjust the green LED error flag'
            high 3                  'load right-hand-red-LED-ON'
            goto Xxx
x3:         high 1                  'load left-hand-yellow-LED-ON data'
            let w2 = w0 − 10        'get the left tilt outer limit'
            if w6>w2 then goto Xxx  'if within the limit adjust the green LED error flag'
            high 0                  'load left-hand-red-LED-ON data'
Xxx:        b10=1                      'set the green LED error flag'
bchk:       if pin0 = 0 then goto done  'if button held down stop data acquisition'
            gosub Zgo                  'call the next Z axis routine'
Ygo:        low 4                   'switch OFF the Y axis LEDs only'
            low 5                   'switch OFF the Y axis LEDs only'
            low 6                   'switch OFF the Y axis LEDs only'
            low 7                   'switch OFF the Y axis LEDs only'
            peek $C2,b0             'fetch Yaxis LSB docking value from cold storage'
            peek $C3,b1             'fetch Yaxis MSB docking value from cold storage'
            readadc10 1, w6         'get new Y axis data into w6'
y1:         let w1=w0+4             'calculate inner limits'
            let w2=w0−4             'calculate inner limits'
            if w6>=w1 then goto y2  'if back tilt skip to y2'
            if w6<=w2 then goto y3  'if forward tilt skip to y3'
            b11=0                      'clear the green LED error flag'
            goto Yend
y2:         high 5                  'load top-yellow-LED-ON data'
            let w1=w0+10            'get the back tilt outer limit'
            if w6<w1 then goto Yyy  'if within the limit adjust the green LED error flag'
            high 4                  'load top-hand-red-LED-ON'
            goto Yyy
y3:         high 6                  'load bottom-yellow-LED-ON data'
            let w2 = w0−10          'get the forward tilt outer limit'
            if w6>w2 then goto Yyy  'if within the limit adjust the green LED error flag'
            high 7                  'load bottom-red-LED-ON data'
```

-continued

```
Yyy:        b11=1                                'set the green LED error flag'
Yend:       goto main                            'keep going'
done:       sertxd ("Test complete ",13,10)
            gosub send
            let pinsc = %00000000                'switch off Z axis LEDs'
            let pins = %00000000                 'switch off X and Y axis red LEDs'
            end
'*************************main data acquisition routine completed*****************************'
'*****************************Z axis sub-routine *********************************************'
Zgo:        peek $C4,b0                          'fetch Zaxis LSB docking value from cold storage'
            peek $C5,b1                          'fetch Zaxis MSB docking value from cold storage'
            peek $C6,b2                          'fetch Zaxis LSB NBTL from cold storage'
            peek $C7,b3                          'fetch Zaxis MSB NBTL from cold storage'
            peek $C8,b4                          'fetch Zaxis LSB NBBL from cold storage'
            peek $C9,b5                          'fetch Zaxis MSB NBBL from cold storage'
            for b8=1 to 25                       'start Z axis loop counter'
            readadc10 2,w6                       'acquire Z axis analog signal'
            if w6<=w1 AND w6>=w2                 'if within the boundary limits skip error routine'
            then goto rep1
            let w3 = w3+w6                       'else, add new value to the error register'
            let w3 = w3−w2                       'subtract the docking value to get the net accumulated error'
rep1:       next b8                              'continue data acquisition until 25 loops complete'
            let w3 = w3+0                        'apply correction value if necessary'
            let pinsc = %00000000                'switch off all Z axis LEDs'
            if w3<32738 then goto z1             'test data; if counterclockwise error, goto to red/yellow tests'
            if w3>32898 then goto z2             'if clockwise error goto red/yellow tests'
            let w3 = 32768                       'alignment OK, check the green LED error flags'
            if b10=1 OR b11=1 then               'if Xaxis or Yaxis not correct skip to end of subroutine'
            goto Zzz
            high portc 3                         'switch ON green LED'
            goto Zzz                             'skip to end of subroutine'
z1:         high portc 5                         'small counterclkwise Z axis error, show yellow LED'
            if w3>31768 then goto Zzz            'if not large counterclockwise error, skip to end of subroutine'
            high portc 4                         'large counterclkwise Z axis error, show red LED'
            goto Zzz                             'skip to end of subroutine'
z2:         high portc 6                         'small clockwise Z axis error, show yellow LED'
            if w3<33768 then goto Zzz            'if not large clockwise error, skip to end of subroutine'
            high portc 7                         'large clockwise Z axis error, show red LED'
Zzz:        return                               'end of subroutine'
'***************************Z axis sub-routine completed**************************************'
'***Subroutine for push button operation *****'
pbtn:       if pin0 = 1 then goto pbtn           'wait for button to be pushed'
            high portc 3                         'switch ON green LED'
            pause 50                             'pause 50mSecs for switch debounce'
pbt1:       if pin0 = 0 then goto pbt1           'wait for button to be released'
            low portc 3                          'switch OFF greed LED'
            return
'************************Subroutine for sending data to terminal *****************************'
send:       peek $C0,b0                          'fetch Xaxis LSB docking value from cold storage'
            peek $C1,b1                          'fetch Xaxis MSB docking value from cold storage'
            sertxd("Roll = ",#w0," ")
            peek $C2,b0                          'fetch Yaxis LSB docking value from cold storage'
            peek $C3,b1                          'fetch Yaxis MSB docking value from cold storage'
            sertxd("Pitch = ",#w0," ")
            peek $C4,b0                          'fetch Zaxis LSB docking value from cold storage'
            peek $C5,b1                          'fetch Zaxis MSB docking value from cold storage'
            sertxd("Rotation = ",#w0," ")
            sertxd("Total Error = ",#w3,13,10)
            return
```

The claims defining the invention are as follows:

1. A surgical orientation system for assisting a surgeon to orient a prosthetic component relative to a patient's anatomy, the system including:

an implement for releasable attachment of a prosthetic component;

an electronic orientation monitor attachable to the implement; and an brace for releasable attachment to an external portion of the patient so as to define a reference point relative to said anatomy, said reference point being disposed in use externally of the patient and being adapted for orientation of the electronic orientation monitor into a reference orientation;

wherein the electronic orientation monitor is adapted to acquire reference orientation information whilst in said reference orientation; and wherein said electronic orientation monitor is adapted to acquire subsequent orientation information during manipulation of the implement whilst the implement is physically separate from the brace.

2. A surgical orientation system according to claim 1, wherein the electronic orientation monitor is adapted to acquire subsequent orientation information during manipulation of the implant.

3. A surgical orientation system according to claim 1, wherein the electronic orientation monitor includes at least one of an inertial sensor; an accelerometer; a gyroscope; a magnetometer and/or an inclinometer.

4. A surgical orientation system according to claim 1, wherein the reference point includes a surface defining a reference plane.

5. A surgical orientation system according to claim 4, wherein the surface is part of a docking station adapted to receive the electronic orientation monitor and to thereby orient the electronic orientation monitor into the reference orientation.

6. A surgical orientation system according to claim 5, wherein the docking station is rotatably disposed on the brace.

7. A surgical orientation system according to claim 1, wherein the brace includes a movable jaw for clamping engagement with the patient.

8. A surgical orientation system according to claim 7, wherein the movable jaw is disposed at a rear end of the brace, the movable jaw having at least one rear positioning pad for clamping engagement adjacent the patient's sacrum.

9. A surgical orientation system according to claim 8, further including at least one front positioning pad disposed at a front end of the brace for clamping engagement adjacent the patient's pubic crest.

10. A surgical orientation system according to claim 9, including two further front positioning pads disposed at the front end of the brace for clamping engagement adjacent the patient's anterior superior iliac spine.

11. A surgical orientation system according to claim 10, wherein the docking station is rotatably disposed on the brace, and wherein the rotatable docking station defines an axis of rotation that is parallel to a plane containing the at least one front positioning pad and the two further front positioning pads.

12. A surgical orientation system according to claim 9, wherein the brace includes a base extending intermediate and interconnecting the front end and the rear end, said base being adapted in use to at least partially support the patient.

13. A surgical orientation system according to claim 9, wherein the brace includes an elongate frame extending intermediate and interconnecting the front end and the rear end, said elongate frame being adapted in use for disposition between the patient's legs.

14. A method of assisting a surgeon to orient a prosthetic component relative to a patient's anatomy, said method including the steps of:
providing an implement for releasable attachment of a prosthetic component, said implement having an electronic orientation monitor disposed thereon;
releasably attaching an external portion of the patient to an brace so as to define a reference point relative to said anatomy, said reference point being disposed in use externally of the patient;
using the reference point to orient the electronic orientation monitor into a reference orientation;
using the electronic orientation monitor to acquire reference orientation information whilst in the reference orientation;
manipulating the implement such that the prosthetic component is adjacent said anatomy; and
using the electronic orientation monitor to provide an indication when a subsequent orientation of the electronic orientation monitor has a predefined relationship relative to the reference orientation.

15. A method according to claim 14, further including the step of using the electronic orientation monitor to provide an indication so as to guide manipulation of the implement such that a subsequent orientation of the electronic orientation monitor is guided towards the predefined relationship relative to the reference orientation.

16. A method according to claim 14, further including a step of ascertaining a neutral pelvic tilt angle of the patient's pelvis and rotating the reference point by an angle corresponding to said neutral pelvic tilt angle.

17. A method according to claim 16, wherein the step of ascertaining a neutral pelvic tilt angle of the patient's pelvis includes forming an x-ray image of the patient's pelvis as viewed from the side and ascertaining from the x-ray image an angle between a line representing the vertical and a line extending from the patient's anterior superior iliac spine to the patient's pubic crest.

18. A surgical orientation system for assisting a surgeon to orient a prosthetic component relative to a patient's anatomy, the system including:
an implement for releasable attachment of a prosthetic component;
an electronic orientation monitor attachable to the implement; and
an brace for releasable attachment to an external portion of the patient so as to define a reference point relative to said anatomy in a region adjacent the external portion of the patient, said reference point being disposed in use externally of the patient and being adapted for orientation of the electronic orientation monitor into a reference orientation;
wherein the electronic orientation monitor is adapted to acquire reference orientation information while in said reference orientation; and
wherein said electronic orientation monitor is adapted to acquire subsequent orientation information during manipulation of the implement whilst the implement is physically separate from the brace.

* * * * *